(12) United States Patent
Kudo et al.

(10) Patent No.: US 8,500,709 B2
(45) Date of Patent: Aug. 6, 2013

(54) ABSORBENT ARTICLE

(75) Inventors: Jun Kudo, Kagawa (JP); Hideyuki Kinoshita, Kagawa (JP); Akira Hashino, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 865 days.

(21) Appl. No.: 12/593,744

(22) PCT Filed: Jan. 25, 2008

(86) PCT No.: PCT/JP2008/051106
§ 371 (c)(1),
(2), (4) Date: Jan. 8, 2010

(87) PCT Pub. No.: WO2008/126442
PCT Pub. Date: Oct. 23, 2008

(65) Prior Publication Data
US 2010/0121303 A1 May 13, 2010

(30) Foreign Application Priority Data
Mar. 30, 2007 (JP) .................................. 2007-093742

(51) Int. Cl.
*A61F 13/15* (2006.01)
*A61F 13/20* (2006.01)
(52) U.S. Cl.
USPC ............................. 604/385.101; 604/385.01
(58) Field of Classification Search
USPC ................. 604/385.01, 367, 385.101, 385.04
See application file for complete search history.

(56) References Cited

U.S. PATENT DOCUMENTS

| 6,464,677 | B1 | 10/2002 | Noguchi et al. |
| 6,471,682 | B2 | 10/2002 | Kashiwagi |
| 6,652,498 | B1 | 11/2003 | Glasgow et al. |
| 6,676,649 | B2 | 1/2004 | Mizutani |
| 6,805,691 | B2 | 10/2004 | Kashiwagi et al. |
| 2002/0143309 | A1 | 10/2002 | Glasgow et al. |

(Continued)

FOREIGN PATENT DOCUMENTS

| EP | 0985396 A2 | 3/2000 |
| EP | 1 080 708 A2 | 3/2001 |

(Continued)

OTHER PUBLICATIONS

PCT/JP2008/051106 International Search Report.

(Continued)

*Primary Examiner* — Michele M Kidwell
(74) *Attorney, Agent, or Firm* — Lowe Hauptman Ham & Berner, LLP

(57) ABSTRACT

An absorbent article that is worn by a user, including: a main body section of the absorbent article; an absorbent body that includes an absorbent member absorbing liquid, that has a longitudinal direction, a width direction, and a thickness direction, that is superposed on a user side of the main body section, whose one end section of the longitudinal direction is joined to the main body section at a first joined section, and whose another end section of the longitudinal direction is joined to the main body section at a second joined section; and a restricting member that is disposed between the first joined section and the second joined section in the longitudinal direction, and that restricts relative shifting between the main body section and the absorbent body when the main body section and the absorbent body that are superposed are folded.

12 Claims, 21 Drawing Sheets

U.S. PATENT DOCUMENTS

| | | | |
|---|---|---|---|
| 2006/0282059 A1* | 12/2006 | Fujikawa et al. | 604/385.17 |
| 2010/0076392 A1 | 3/2010 | Kudo | |
| 2010/0106125 A1 | 4/2010 | Kudo et al. | |
| 2010/0145296 A1 | 6/2010 | Kudo et al. | |

FOREIGN PATENT DOCUMENTS

| | | |
|---|---|---|
| EP | 1 097 685 A3 | 8/2001 |
| EP | 1132066 A1 | 9/2001 |
| EP | 1245211 A2 | 10/2002 |
| EP | 1327429 A2 | 7/2003 |
| EP | 2044914 A1 | 4/2009 |
| EP | 2092917 A1 | 8/2009 |
| EP | 2127620 A1 | 12/2009 |
| JP | 53-97540 | 8/1978 |
| JP | 7-33315 U | 6/1995 |
| JP | 11-104168 A | 4/1999 |
| JP | 2001-061885 A | 3/2001 |
| JP | 2001-314439 A | 11/2001 |
| JP | 2004-188115 A | 7/2004 |

OTHER PUBLICATIONS

European extended search report dated Dec. 1, 2011.
Australian Office Action for Application No. 2008238678 mailed Aug. 2, 2012.

* cited by examiner

A-A CROSS SECTION

B-B CROSS SECTION

C-C CROSS SECTION

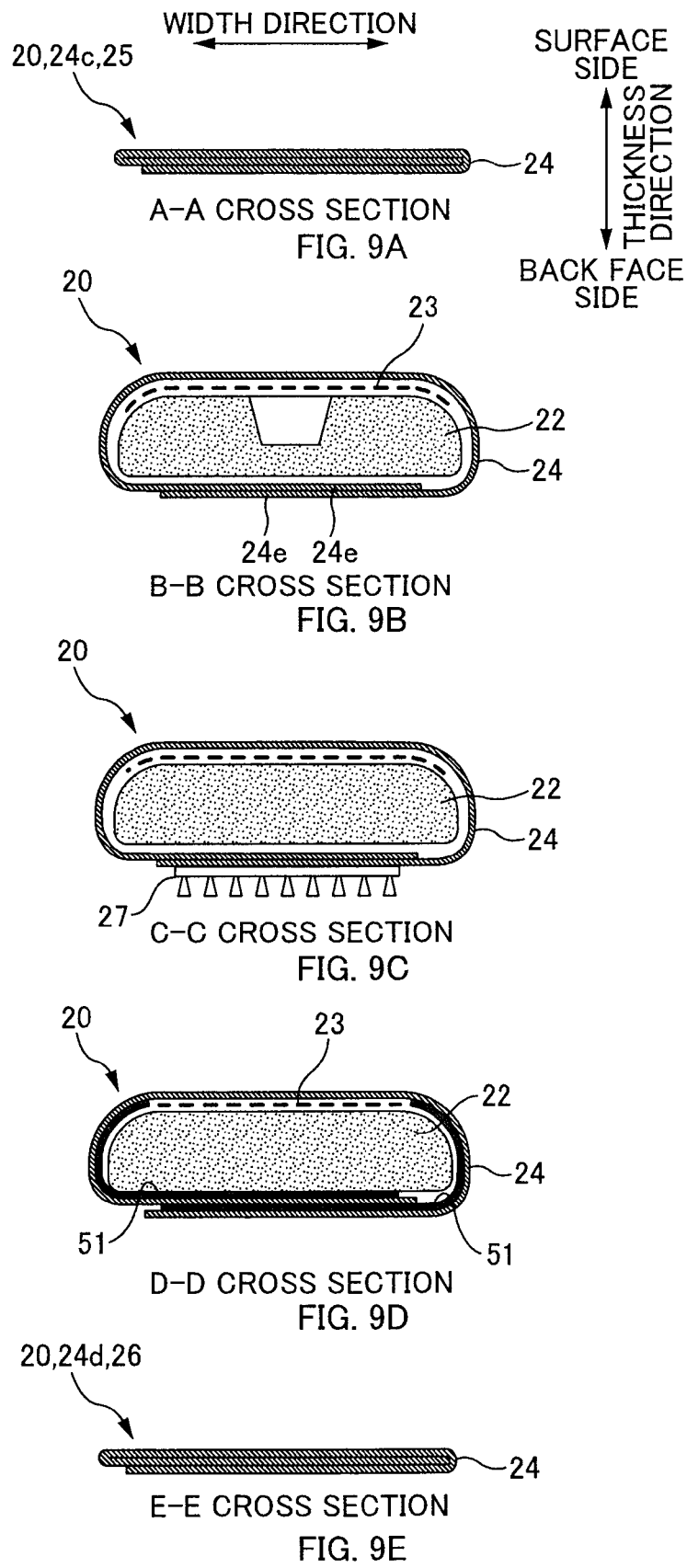

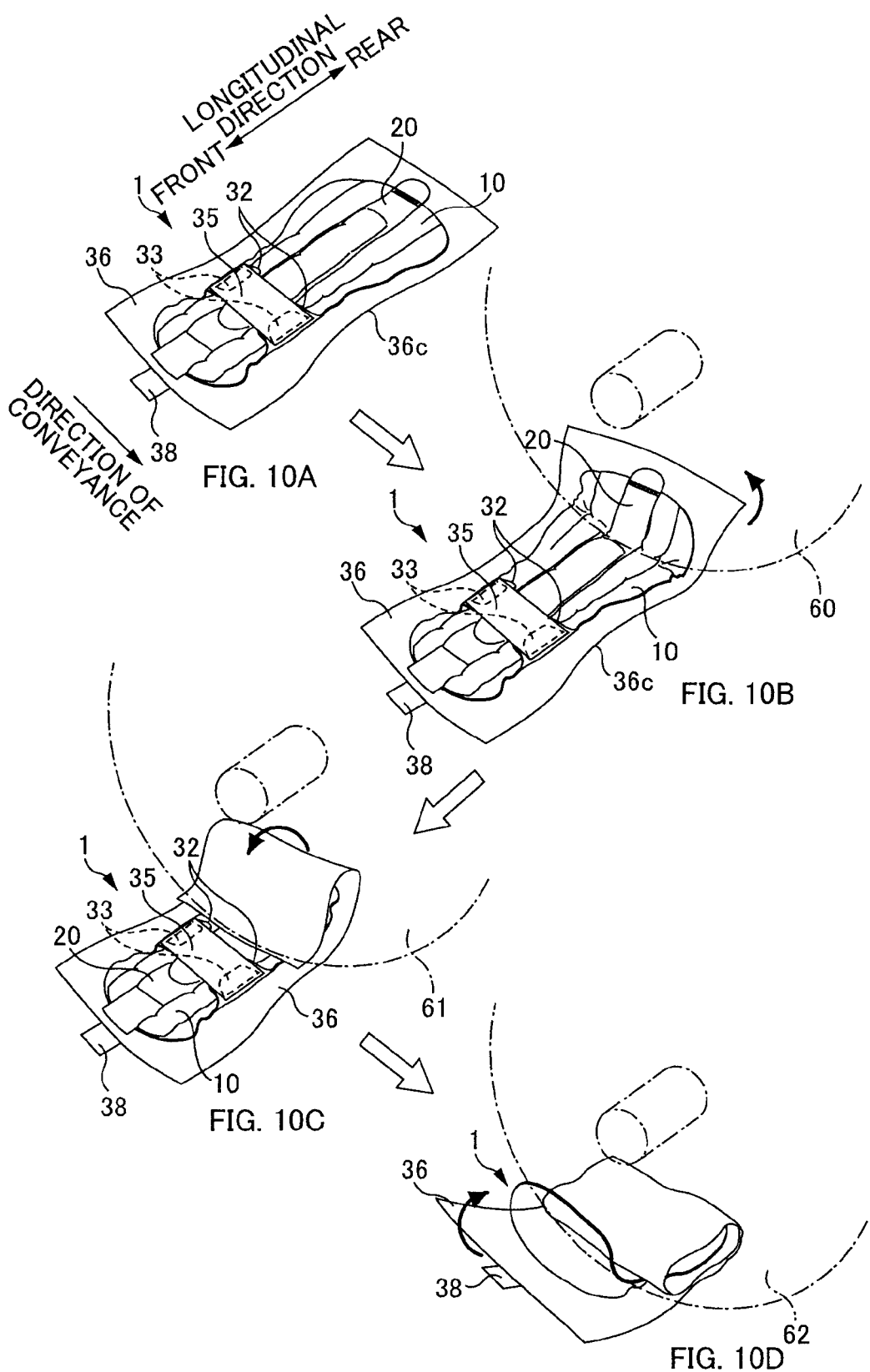

ABSORBENT ARTICLE

RELATED APPLICATIONS

The present application is based on International Application PCT/JP2008/051106, filed Jan. 25, 2008, which claims priority from Japan Application Number 2007-93742, filed Mar. 30, 2007, the disclosures of which are hereby incorporated by reference herein in their entirety.

TECHNICAL FIELD

The present invention relates to absorbent articles that absorb liquid.

BACKGROUND ART

Absorbent articles have conventionally been known that include an absorbent body absorbing certain liquid such as menstrual blood. Among such absorbent articles are those having a two-layered structure including, for example, a first absorbent body (main body section) that absorbs liquid and a second absorbent body (absorbent body) superposed on the first absorbent body (e.g., see JP-A-11-104168). Normally, an absorbent article having a two-layered structure is folded with the face of the absorbent article that contacts a user's body placed on the inside, and wrapped individually.

DISCLOSURE OF INVENTION

Problems to be Solved by Invention

Absorbent articles having the above-mentioned two-layered structure have a problem that even if both ends of the longitudinal direction of the first and second absorbent bodies are joined, when the first and second absorbent bodies are separable anywhere except at the ends, the first and second absorbent bodies relatively shift from each other when folded, so that the second absorbent body is folded shifting from its attachment position on the first absorbent body.

The invention has been made based on the conventional problem as described above, and an advantage thereof is to provide an absorbent article that prevents the main body section and the absorbent body from relatively shifting from each other when folded.

Means for Solving Problems

In order to solve the above-described problems, a primary aspect of the invention is an absorbent article that is worn by a user, including: a main body section of the absorbent article; an absorbent body that includes an absorbent member absorbing liquid, that has a longitudinal direction, a width direction, and a thickness direction, that is superposed on a user side of the main body section, whose one end section of the longitudinal direction is joined to the main body section at a first joined section, and whose another end section of the longitudinal direction is joined to the main body section at a second joined section; and a restricting member that is disposed between the first joined section and the second joined section in the longitudinal direction, and that restricts relative shifting between the main body section and the absorbent body when the main body section and the absorbent body that are superposed are folded.

Effect Of Invention

According to the invention, it is possible to provide an absorbent article that prevents the main body section and the absorbent body from relatively shifting from each other when folded.

BRIEF DESCRIPTION OF DRAWINGS

[FIG. 7]

[FIG. 9] FIGS. 9A to 9E are cross-sectional views taken along the lines A-A, B-B, C-C, D-D, and E-E in FIG. 8, respectively.

[FIG. 10] This is a diagram illustrating a procedure in which the sanitary napkin to be wrapped is folded.

LIST OF REFERENCE NUMERALS

Figure 1:
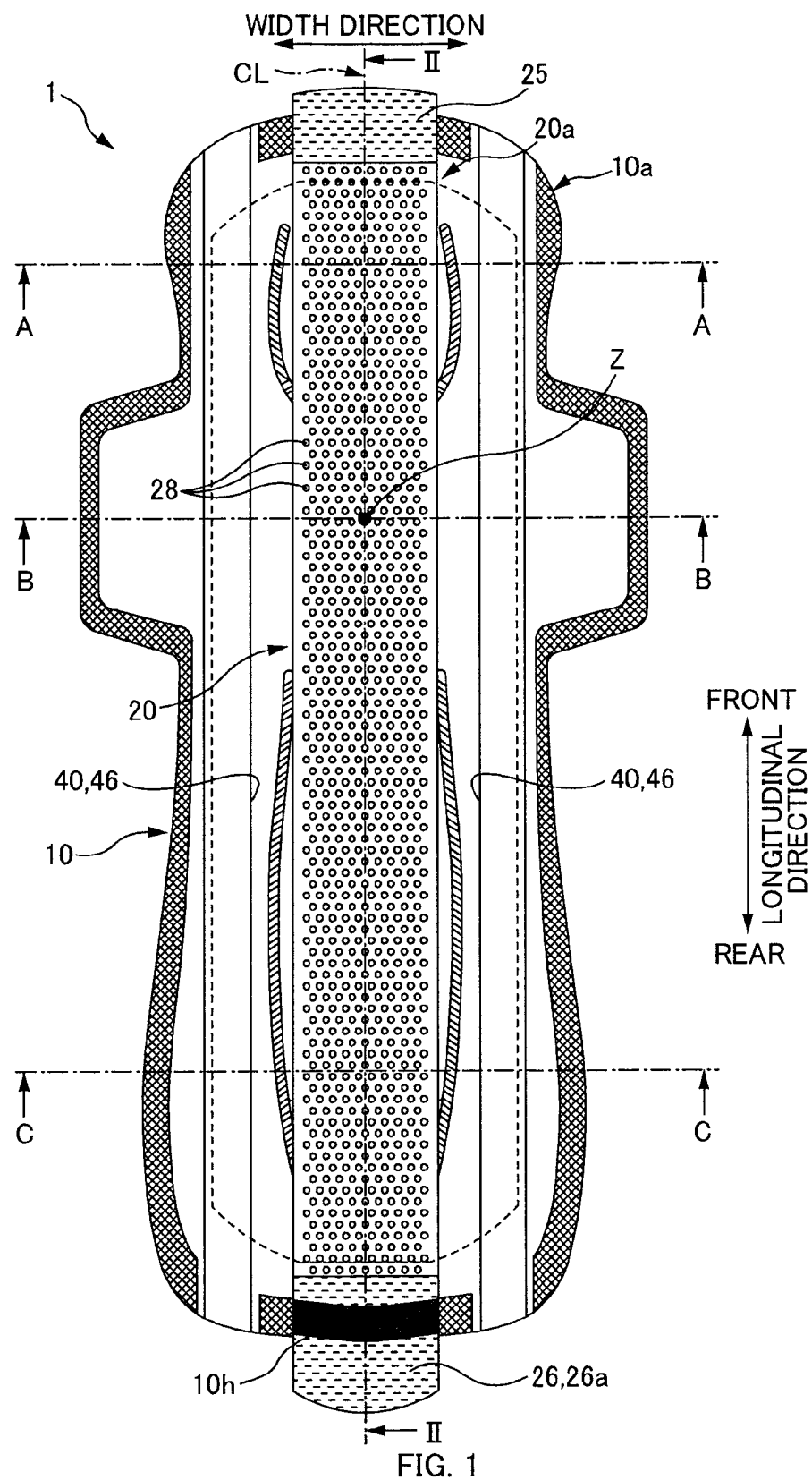
[FIG. 1] This is a developed plan view of the surface side of a sanitary napkin.

1: sanitary napkin (absorbent article), 10: base absorbent body (absorbent body), 10a: front end section, 10b: rear end section, 10g: first joined section, 10h: second joined section, 10i: first joined section, 10j: base absorbent body, 12: absorbent-body base material, 12a: pulverized-pulp layered body, 14: surface sheet, 15: compressed channel, 20: top absorbent body (main body section), 20a: front end section, 20b: rear end section, 22: pulverized-pulp layered body (absorbent member), 23: intermediate sheet, 24: shape-keeping sheet, 25: sealed section, 26: sealed section, 27: fastening section (temporary-joining restricting section), 28: opening, 30: back face sheet, 30a: front end section, 30b: rear end section, 31: shift-prevention attaching section, 32: holding section, 33: shift-prevention attaching section, 34: protection sheet, 35: protection sheet (sheet), 36: wrapping sheet, 38: tape, 39 rear holding section, 40: side sheet, 44: fixed section, 46: end section, 48: elastic member, 51: leakage-prevention sheet, 60: first disk, 61: second disk, 62: third disk, 70: protection sheet (sheet), 71: shift-prevention attaching section, 76: adhesive, 90: undergarment, CL: center line, Z: position that is assumed to face the vaginal opening

BEST MODE FOR CARRYING OUT THE INVENTION

At least the following matters are disclosed in the description of the present specification and reference to the accompanying drawings.

An absorbent article that is worn by a user, including: a main body section of the absorbent article; an absorbent body that includes an absorbent member absorbing liquid, that has a longitudinal direction, a width direction, and a thickness direction, that is superposed on a user side of the main body section, whose one end section of the longitudinal direction is joined to the main body section at a first joined section, and whose another end section of the longitudinal direction is joined to the main body section at a second joined section; and a restricting member that is disposed between the first joined section and the second joined section in the longitudinal direction, and that restricts relative shifting between the main body section and the absorbent body when the main body section and the absorbent body that are superposed are folded.

With such an absorbent article, the restricting member can restrict the relative shifting of the main body section and absorbent body between the first joined section and the second joined section, when the absorbent article is folded with the main body section and absorbent body being superposed. Therefore, it is possible to prevent the absorbent body from being folded shifting from its attachment position on the main body section. For example, when the absorbent article is folded and individually wrapped, it is possible to prevent the absorbent article from being folded with the absorbent body slanting relative to the longitudinal direction of the main body section.

In such an absorbent article, a folding position is between the first joined section and the restricting member, or between the second joined section and the restricting member.

With such an absorbent article, when the main body section and the absorbent body are folded at the folding position, their portions close to the first joined section with respect to the folding position can be prevented from shifting relatively by the first joined section and their portions close to the restricting member with respect to the folding position can be prevented from shifting relatively by the restricting member. Also, when the main body section and the absorbent body are folded at the folding position, their portions close to the second joined section with respect to the folding position can be restricted from shifting relatively by the second joined section and their portions close to the restricting member with respect to the folding position can be restricted from shifting relatively by the restricting member.

In such an absorbent article, a plurality of the restricting members are disposed between the first joined section and the second joined section in the longitudinal direction, and a folding position is between the plurality of restricting members in the longitudinal direction.

With such an absorbent article, when the main body section and the absorbent body are folded at the folding position, the relative shifting between them can be restricted by the restricting members.

In such an absorbent article, the main body section includes a holding section protruding in the width direction, the holding section is folded in towards the absorbent body, a sheet bonds releasably with a face on the user side of the holding section that is folded, the sheet and the main body section hold the absorbent body therebetween, portions of the sheet and the main body section that hold the absorbent body therebetween restrict the relative shifting as the restricting members, and the holding section maintains an attachment position of the main body section with respect to clothing when the absorbent article is worn.

With such an absorbent article, the relative shifting between the main body section and the absorbent article can be restricted by holding the absorbent article between the main body section and the sheet. Also, the holding section, which prevents the absorbent article from being displaced with respect to clothing when the absorbent article is worn, can be used as a part of the restricting member. That is, it is not necessary to separately include a restricting member that is only for the purpose of preventing the relative shifting between the main body section and the absorbent body.

In such an absorbent article, a temporary-joining restricting section that joins the main body section and the absorbent body in a re-joinable manner is disposed between the first joined section and the second joined section in the longitudinal direction, and the temporary-joining restricting section restricts the relative shifting as the restricting member.

With such an absorbent article, separating the main body section and absorbent body allows the position of the absorbent body to be adjusted when the absorbent body is worn, even after the relative shifting between the main body section and absorbent body when folded has been restricted by the temporary-joining restricting section. In addition, the main body section and the absorbent body can be re-joined by the temporary-joining restricting section at the adjusted position of the absorbent body, and the absorbent body is held at an appropriate position when worn. Similarly to the holding section, the temporary-joining restricting section for keeping the position of the absorbent body relative to the main body section can be used as the restricting member, and therefore it is not necessary to separately include a restricting member that is only for the purpose of preventing the relative shifting between the main body section and the absorbent body.

In such an absorbent article, a temporary-joining restricting section that joins the main body section and the absorbent body in a re-joinable manner is disposed between the first joined section and the second joined section in the longitudinal direction, the temporary-joining restricting section restricts the relative shifting as the restricting member, the portions of the sheet and the main body section that hold the absorbent body therebetween are disposed between the first joined section and the temporary-joining restricting section in the longitudinal direction, a middle folding position is between the portions that hold the absorbent body and the temporary-joining restricting section therebetween in the longitudinal direction, an end-section folding position is between the temporary-joining restricting section and the second joined section in the longitudinal direction, the main body section and the absorbent body are folded at the end-section folding position before being folded at the middle folding position, and the temporary-joining restricting section is disposed closer to the end-section folding position than the middle between the middle folding position and the end-section folding position.

With such an absorbent article, the relative shifting between the main body section and the absorbent article can be reliably prevented when the absorbent article is initially folded at the end-section folding position, even though the relative shifting is likely to occur at the vicinity of the folding position. When the absorbent article is folded at the middle folding position at the second fold, parts of the main body section and absorbent body has already been superposed and folded at the first fold, so the relative shifting between the main body section and the absorbent body is less likely to occur at the second fold than at the first fold. Therefore, there is no problem in disposing the temporary-joining restricting section closer to the end-section folding position.

In such an absorbent article, a temporary-joining restricting section that joins the main body section and the absorbent body in a re-joinable manner is disposed between the first joined section and the second joined section in the longitudinal direction, the temporary-joining restricting section restricts the relative shifting as the restricting member, the portions of the sheet and the main body section that hold the absorbent body therebetween are disposed between the first joined section and the temporary-joining restricting section in the longitudinal direction, a middle folding position is between the portions that hold the absorbent body and the temporary-joining restricting section therebetween in the longitudinal direction, an end-section folding position is between the temporary-joining restricting section and the second joined section in the longitudinal direction, and the temporary-joining restricting section is disposed in the middle between the middle folding position and the end-section folding position.

With such an absorbent article, preventing the relative shifting between the main body section and the absorbent body when the absorbent article is folded at the end-section folding position has the same effect as when the absorbent article is folded at the middle folding position.

Embodiments
General Construction of Sanitary Napkin

Figure 2:
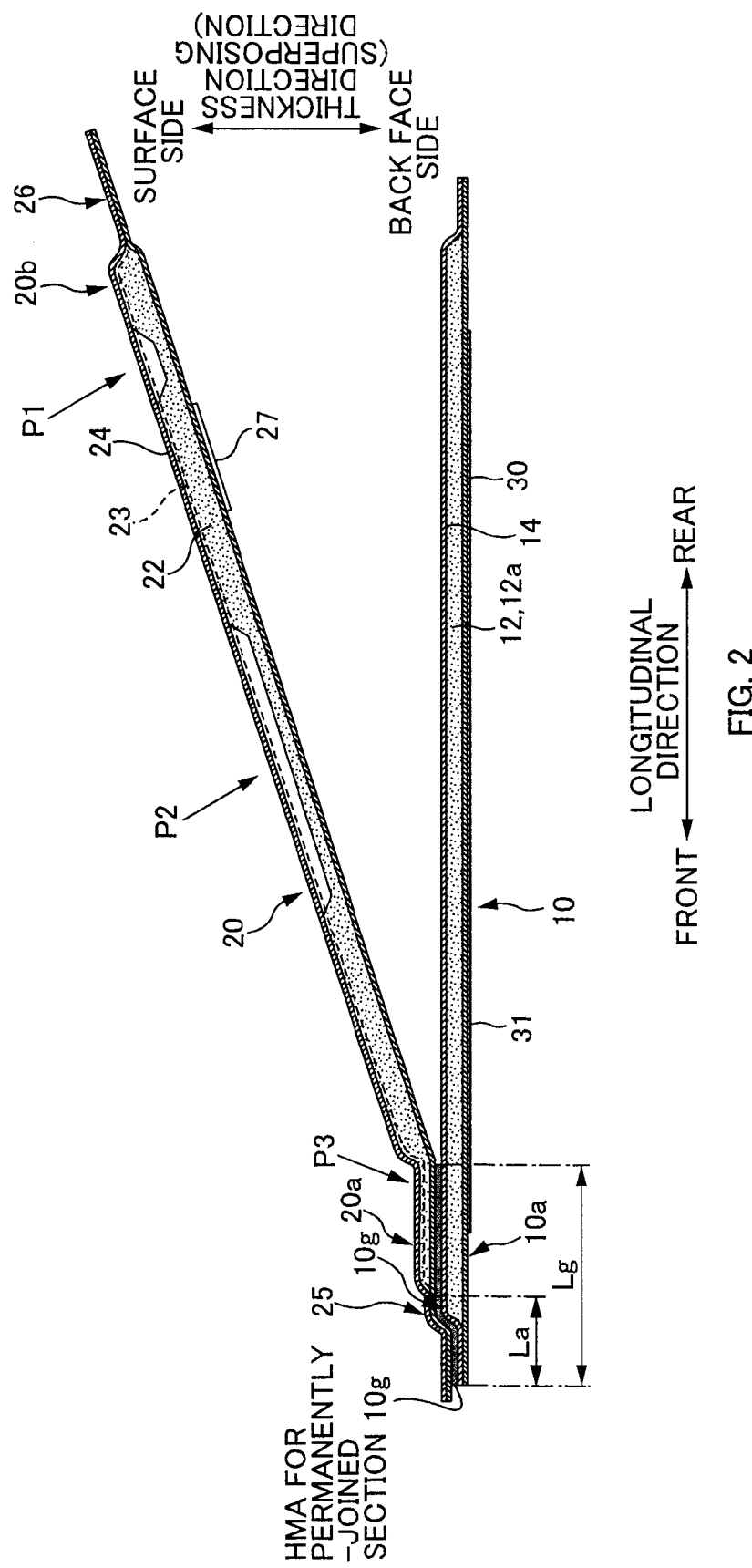
[FIG. 2] This is a cross-sectional view taken along the line II-II in FIG. 1.
Figure 3:
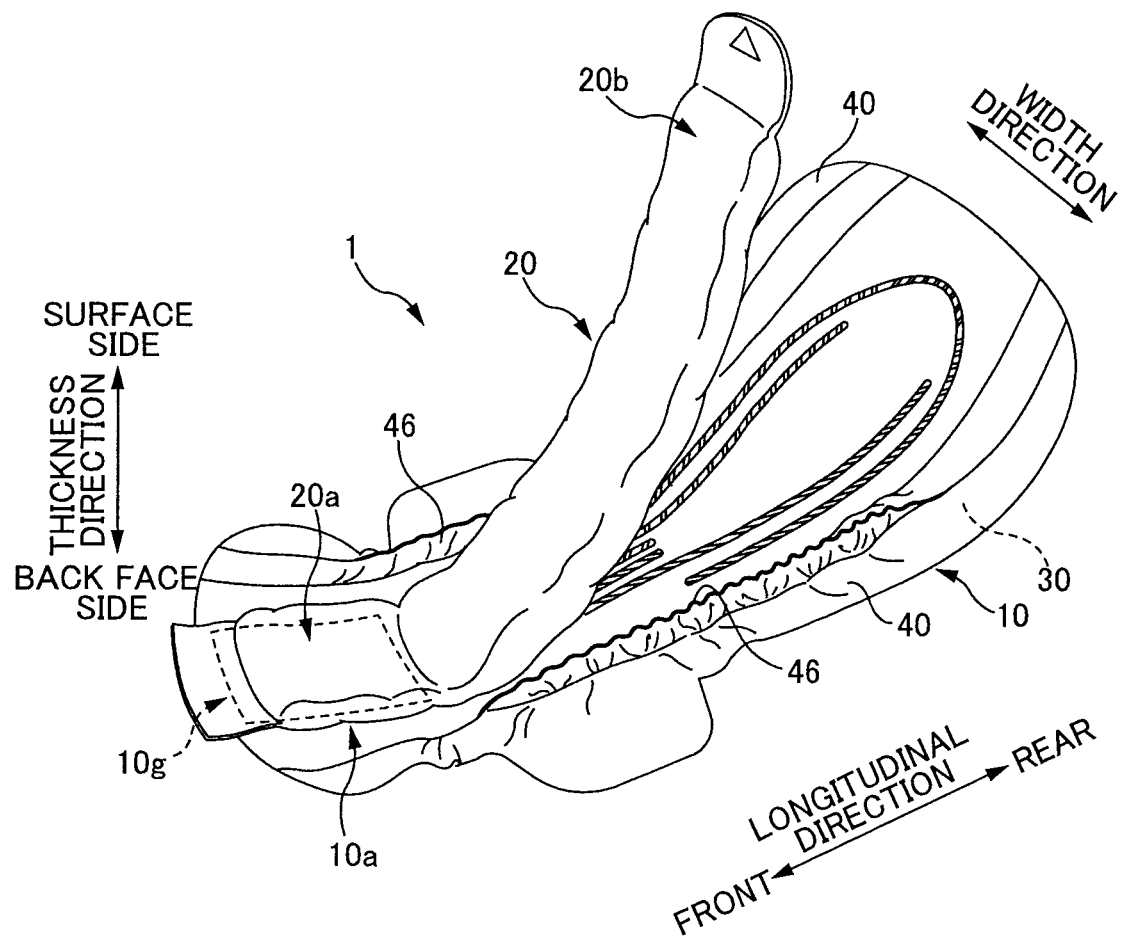
[FIG. 3] This is a perspective view of the sanitary napkin.
Figure 4:
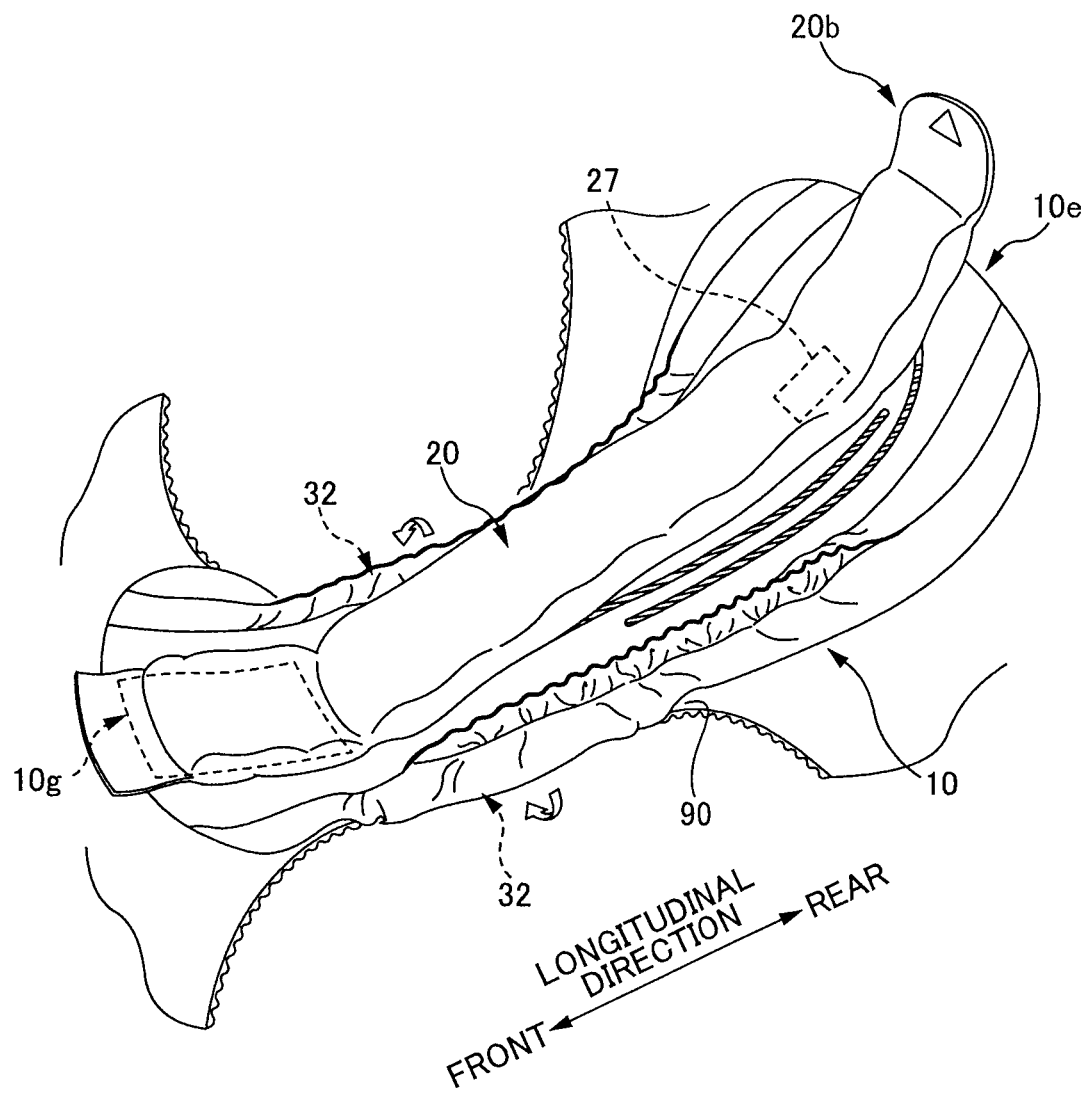
[FIG. 4] This is a perspective view of the sanitary napkin when worn.

In the description below, a sanitary napkin 1 is used as an example of the absorbent article. First, the general construction of the sanitary napkin 1 of the present embodiment will be described. In the following description, the side that contacts the human body is referred to as a surface side, the side that contacts an undergarment 90 (corresponding to the clothes) is referred to as aback face side, the end portion located on the front side of the human body and the end portion located on the rear side of the human body when the sanitary napkin 1 is worn are referred to as a front end section and a rear end section respectively. The direction normal to the surface or back face of the sanitary napkin 1 is referred to as a thickness direction. FIG. 1 is a developed plan view of the surface side of the sanitary napkin 1, and FIG. 2 is a cross-sectional view taken along the line II-II in FIG. 1. Also, FIG. 3 is a perspective view of the sanitary napkin 1 and FIG. 4 is a perspective view of the sanitary napkin 1 when worn.

This sanitary napkin 1 includes a base absorbent body 10 (corresponding to the main body section), and a top absorbent body 20 (corresponding to the absorbent body) that is superposed on the surface of the base absorbent body 10 and is disposed along a longitudinal direction in the center of the width direction of the base absorbent body 10. The sanitary napkin 1 has a shape elongated in a predetermined direction as a whole. In the following description, this predetermined direction is referred to as the longitudinal direction, and a direction orthogonal to the longitudinal direction is referred to as the width direction. Note that when the sanitary napkin 1 is worn, the longitudinal direction matches the front-back direction of the human body.

Also, a front end section 20a of the top absorbent body 20 is joined to a front end section 10a of the base absorbent body 10, whereas a rear end section 20b is a free end that can separate from the base absorbent body 10 and move using the front end section 20a as a fulcrum. Therefore, a user of the sanitary napkin 1 first attaches and fixes the base absorbent body 10 to the inner face of the undergarment 90, such that the longitudinal direction thereof is aligned with the front-back direction of the human body, as shown in FIG. 4. Thereafter, in a state in which the undergarment 90 is fitted, the user pulls up the rear end section 20b of the top absorbent body 20 so that the top absorbent body 20 fits into a groove of the buttocks. Then, liquid excreted from the groove such as menstrual blood is absorbed mainly by the top absorbent body 20.

Incidentally, in the sanitary napkin 1, as shown in FIG. 1, a position Z that is assumed to face the vaginal opening (corresponding to the excretory opening of the human body) is positioned on the center line CL of the width direction of the sanitary napkin 1 and on a side closer to the front with respect to the center of the longitudinal direction. That is, the sanitary napkin 1 is formed such that a length of the rear side with respect to the position Z that is assumed to face the vaginal opening is longer than a length of the front side with respect to the position Z.

Next, constituent elements of the sanitary napkin 1 will be described in detail.

Base Absorbent Body 10

Figure 5:
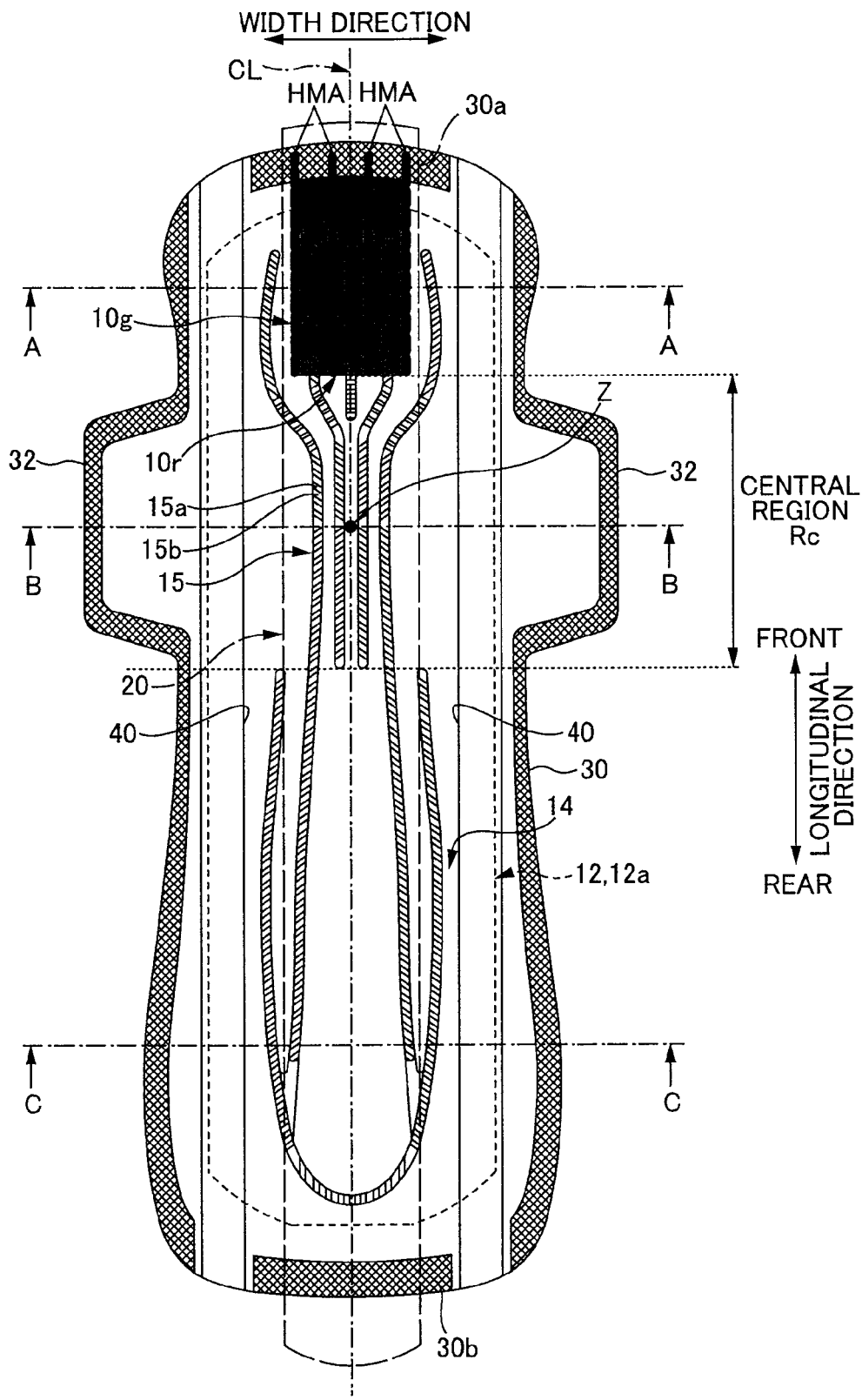
[FIG. 5] This is a plan view of the surface side of a base absorbent body.
Figure 6:
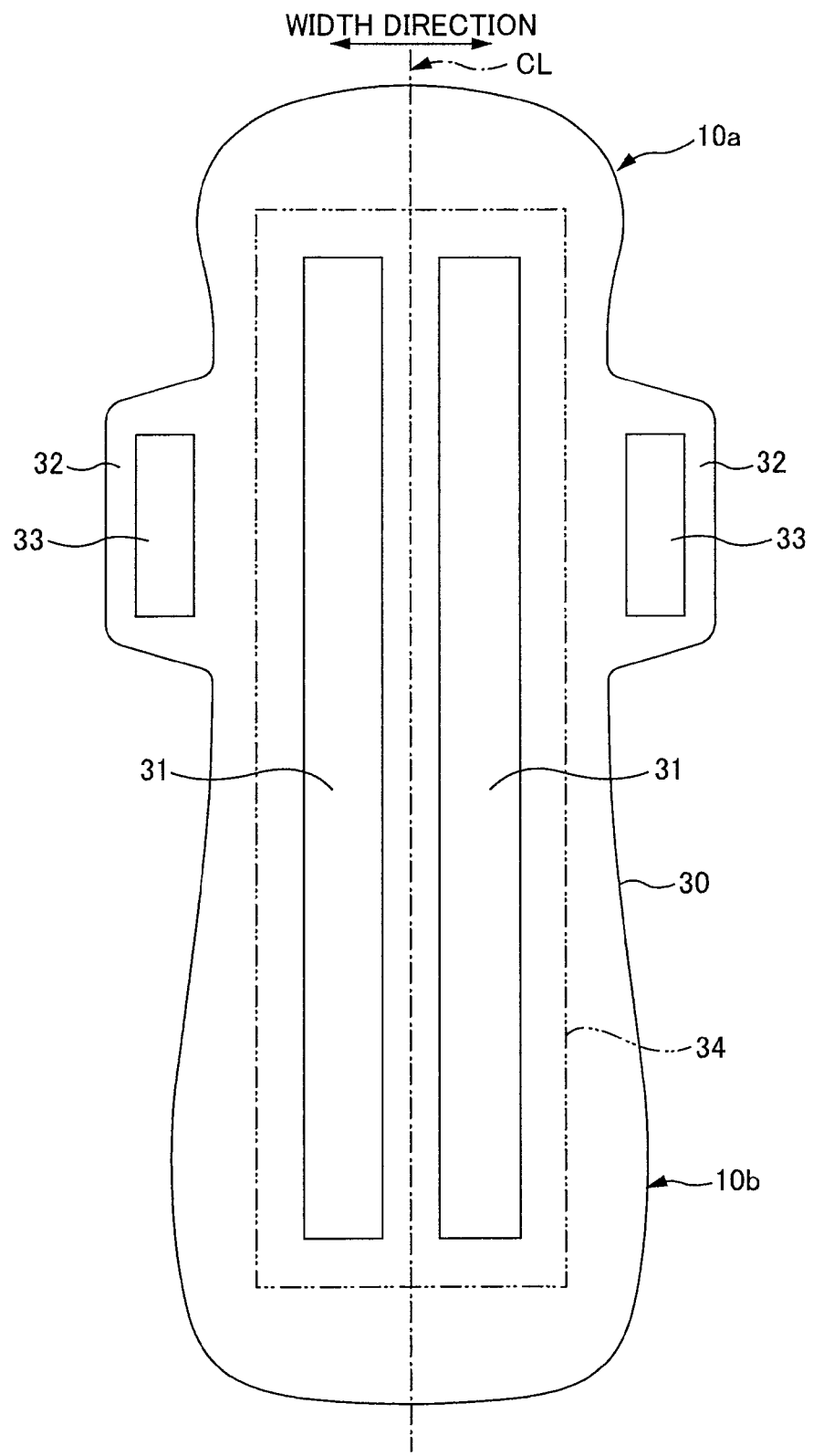
[FIG. 6] This is a plan view of the back face side of the base absorbent body.
Figure 7A:
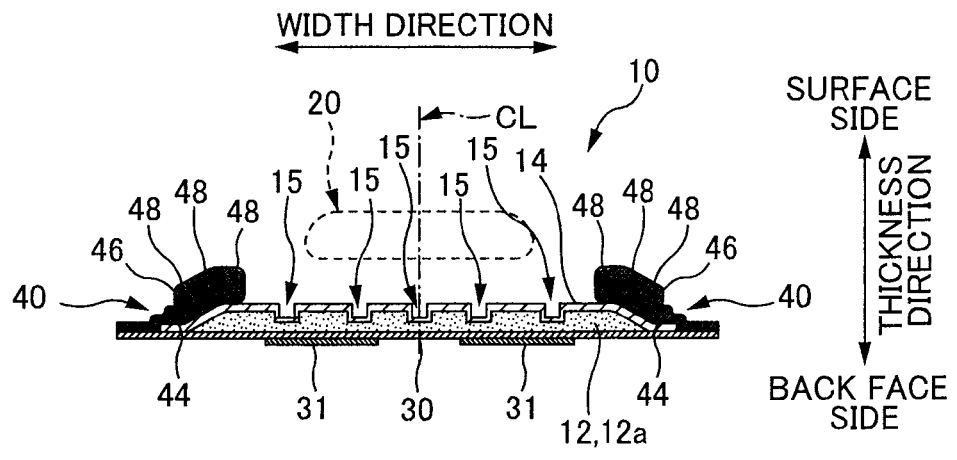
FIGS. 7A to 7C are cross-sectional views taken along the lines A-A, B-B, and C-C in FIG. 5, respectively.
Figure 7B:
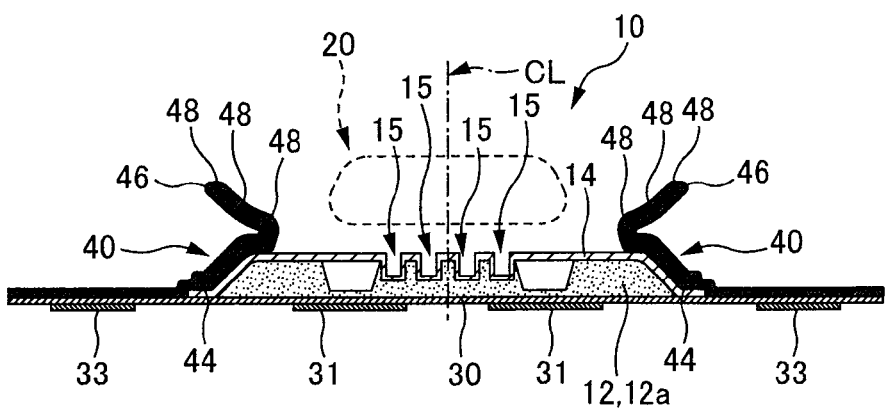
Figure 7C:
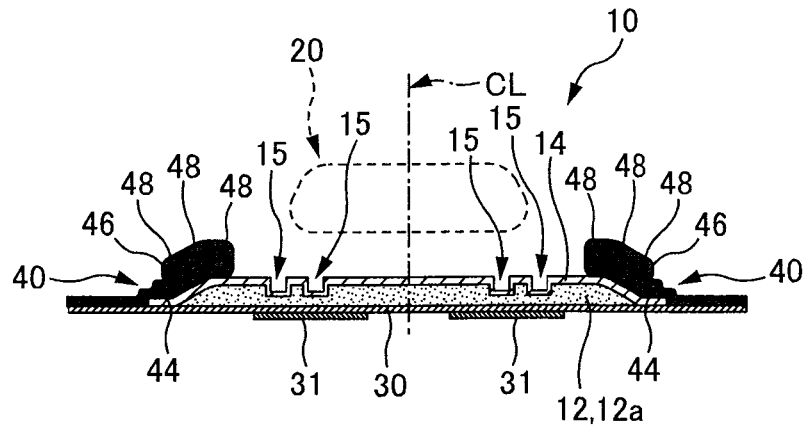

FIG. 5 is a plan view of the surface side of the base absorbent body 10. FIG. 6 is a plan view of the back face side of the base absorbent body 10. FIGS. 7A to 7C are cross-sectional views taken along the lines A-A, B-B and C-C in FIG. 5, respectively. Note that in these diagrams, the top absorbent body 20 is shown in a transparent manner with only the external line thereof being indicated with a dotted line.

The planar shape of the base absorbent body 10 is an approximate rectangle elongated in the longitudinal direction. The base absorbent body 10 includes an absorbent-body base material 12 that absorbs liquid, a surface sheet 14 disposed covering at least the entire face of the surface side of the absorbent-body base material 12, a back face sheet 30 that prevents liquid absorbed by the absorbent-body base material 12 from leaking to the back face side, and side sheets 40 for forming leakage-prevention walls 46 that prevent liquid from leaking to the outer sides of the width direction.

The absorbent-body base material 12 includes a pulverized-pulp layered body 12a formed by layering pulverized pulp made up of pulp which is pulverized, superabsorbent polymer mixed into the pulverized-pulp layered body 12a, and a fluid-permeable sheet (not shown) such as tissue paper that wraps the pulverized-pulp layered body 12a.

The surface sheet 14 is a fluid-permeable sheet. The material of the surface sheet 14 is an appropriate nonwoven fabric or the like; for example, a through-air nonwoven fabric, a spunlace nonwoven fabric and the like made up of a plastic fiber such as polyester or polyethylene undergo a hydrophilic treatment etc. and are used.

The surface sheet 14 and the absorbent-body base material 12 are compressed in the thickness direction by channel-embossing, with hot-melt adhesive being interposed therebetween. As a result, the surface sheet 14 and the absorbent-body base material 12 are joined and integrated. This channel-embossing is performed using a pair of sandwich-pressing members (not shown) that face each other. One of the pair of sandwich-pressing members includes projections that are located continuously like ribs, and on the peak portions of the rib-like projections, island-shaped projections are formed intermittently in a direction in which the rib-like projections are located continuously. In the other sandwich-pressing member, the face that opposes the rib-like projections is formed flat. Accordingly, in compressed channels 15 formed on the surface sheet 14 and the absorbent-body base material 12 after being subjected to the channel-embossing, low-compression sections 15a compressed at a low compression rate and high-compression sections 15b compressed at a compression rate higher than the low compression rate are alternately formed in directions along which the compressed channels 15 extend, as shown in FIG. 5.

The rigidity of regions where such compressed channels 15 are formed is increased. As shown in FIG. 5, since substantially four compressed channels are formed on the base absorbent body in the longitudinal direction, the base absorbent body 10 is unlikely to deform in the width direction. For example, a central region Rc that has holding sections 32 (described later) protruding in the width direction is in contact with the crotch of the human body and is sandwiched between legs in the width direction. Therefore, when the rigidity of the width direction of the central region Rc is small, the base absorbent body 10 cannot resist being squeezed laterally in the crotch area and is bent along the center line CL. Then, the top absorbent body 20 is sandwiched between both sides of the base absorbent body 10. Due to wrinkles or the like raised along the longitudinal direction in the top absorbent body 20, the attaching properties between the top absorbent body 20 and the groove of the buttocks deteriorate. The compressed channels 15 are formed selectively in regions where such rigidity is required.

The back face sheet 30 is a fluid-impermeable sheet made up of, for example, polyethylene or polypropylene, and has a shape that is longer in the longitudinal direction and wider in the width direction than the absorbent-body base material 12. As shown in FIG. 7B, the absorbent-body base material 12 is attached to the surface side of the back face sheet 30 with hot-melt adhesive, and the back face sheet 30 and the surface sheet 14 are joined by processing such as welding at a front end section 30a and a rear end section 30b shown in FIG. 5. In this manner, the absorbent-body base material 12 is held between the back face sheet 30 and the surface sheet 14. Hot-melt adhesive is preferably interposed between layers of the sheets.

Note that as shown in FIG. 6, on the back face side of the back face sheet 30, "shift-prevention attaching sections 31" are disposed with which the sanitary napkin 1 is attached and fixed to the inner face of the undergarment 90 so that after the sanitary napkin 1 is disposed on the inner face of the undergarment 90, the sanitary napkin 1 does not shift from the disposed position. The shift-prevention attaching sections 31 are, for example, hot-melt adhesive applied over a predetermined range in the back face of the back face sheet 30, and extend from the front end section 10a to a rear end section 10b of the base absorbent body 10.

In order to make prevention of shifting between the undergarment 90 and the sanitary napkin 1 more reliable, the holding sections 32 are formed projecting to the outer side of the width direction of the back face sheet 30 at both ends of the width direction, as shown in FIG. 6. Shift-prevention attaching sections 33 are disposed on the back face of these holding sections 32 as well; the holding sections 32 are folded back to the outside as shown in FIG. 4, and attached and fixed to the outer face of the undergarment 90 with the shift-prevention attaching sections 33. The central position of the longitudinal direction of the holding sections 32 matches the above-described assumed vaginal opening facing position Z.

The side sheets 40 are for forming the leakage-prevention walls 46 at positions close to both sides of the width direction of the absorbent-body base material 12, as shown in FIG. 7B. As shown in FIG. 5, the side sheets 40 are disposed in the longitudinal direction covering the surface sheet 14 from the surface side. The side sheet 40 are made of hydrophobic sheets; as a material thereof, a spunbond nonwoven fabric or the like formed by a plastic fiber such as polypropylene or polyethylene is used, for example.

In more detail, as shown in FIG. 5, a pair of the side sheets 40 is symmetrically disposed with respect to the center line CL of the width direction. The side sheets 40 extend in the longitudinal direction from the front end section 30a to the rear end section 30b of the back face sheet 30, that is, to the external contour of the sanitary napkin 1. As shown in FIG. 7B, the side sheets 40 are pressed and fixed to the surface sheet 14 at the positions close to both sides of the width direction of the absorbent-body base material 12, and fixed sections 44 are formed there. From these fixed sections 44, end sections 46 extend to be a free end. Within these end sections 46, elastic members 48 are fixed being extended in the longitudinal direction. Therefore, when the sanitary napkin 1 is bent such that the surface sheet 14 is on the inner side, the elastic members 48 shrink, and the end sections 46 acting as a free end rise up from the surface sheet 14 so as to be the leakage-prevention walls 46. Also, as shown in FIGS. 7A and 7C, the front end section and the rear end section of the longitudinal direction of the end sections 46, which act as the leakage-prevention walls, are laid down towards the surface sheet 14 and joined to the side sheets 40 with hot-melt adhesive; these end sections form flat sections that do not stand.

Also, these side sheets 40 extend further to the outer sides of the width direction than the fixed sections 44. The outer edge of each side sheet 40 reaches the external contour of the back face sheet 30, namely, the external contour of the sanitary napkin 1. Then, outer edges (see the portions hatched in FIG. 5) are joined with hot-melt adhesive or the like to the outer edges of the width direction of the back face sheet 30 in the longitudinal direction.

Top Absorbent Body 20

Figure 8:
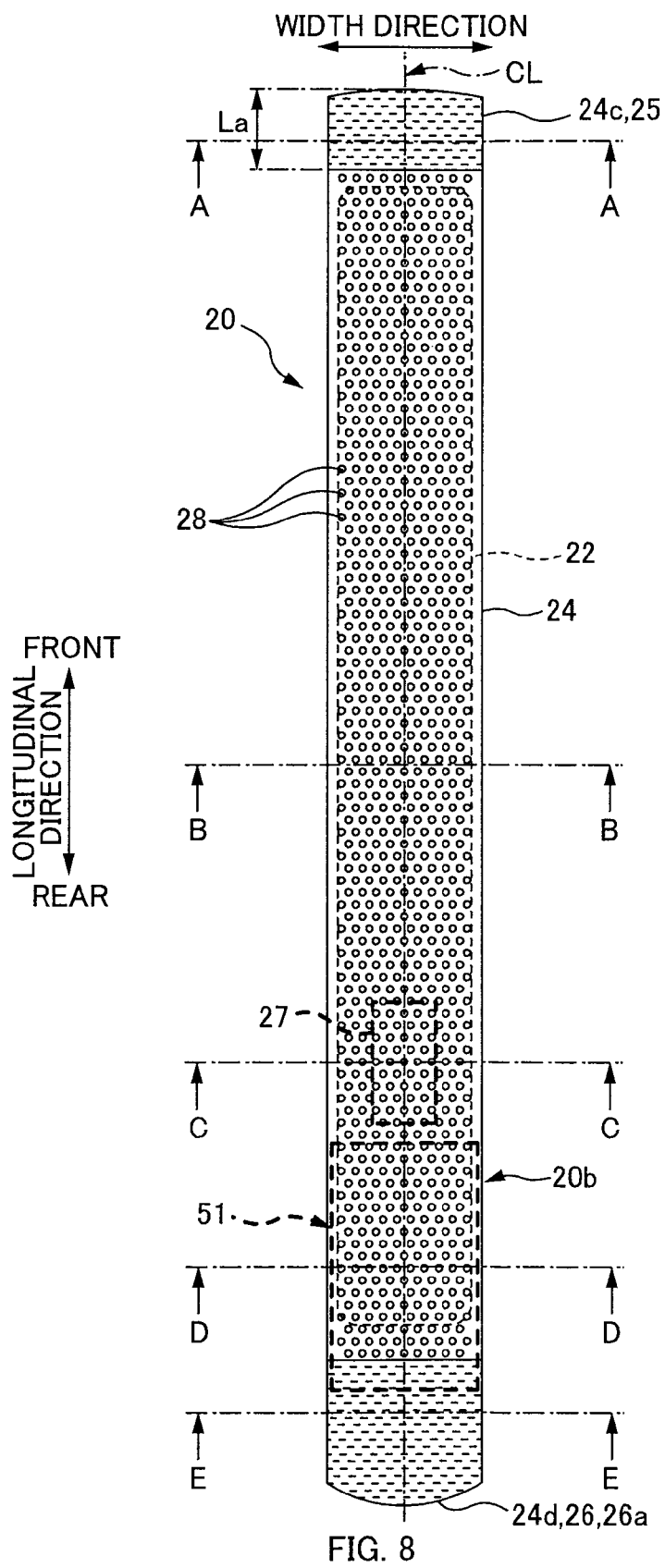
[FIG. 8] This is a developed plan view of a top absorbent body.

FIG. 8 is a developed plan view of the top absorbent body 20. FIGS. 9A to 9E are cross-sectional views taken along the lines A-A, B-B, C-C, D-D and E-E in FIG. 8, respectively.

The top absorbent body 20 includes: a pulverized-pulp layered body 22 that absorbs liquid, an intermediate sheet 23 disposed closer to the surface side than the pulverized-pulp layered body 22, and a shape-keeping sheet 24 which wraps around and holds the pulverized-pulp layered body 22 and the intermediate sheet 23 together and which allows them to retain their shapes elongated in the longitudinal direction.

The intermediate sheet 23 is a fluid-permeable sheet having better liquid drawing properties than the shape-keeping sheet 24; as a material of the intermediate sheet 23, a through-air nonwoven fabric or the like made up of a plastic fiber such as polypropylene is used, for example. With superposed with the shape-keeping sheet 24, the intermediate sheet 23 undergoes perforating embossing and thereby is joined and integrated with the shape-keeping sheet 24.

The perforating embossing is performed using a pair of processing members (not shown) facing each other. Specifically, one of the processing members includes conical projections, and the other processing member that opposes the processing member with projections includes openings into which the conical projections fit. The processing member with the projections formed thereon is heated. These conical projections penetrate the superposed intermediate sheet 23 and shape-keeping sheet 24, to form a large number of openings 28 (see FIG. 1). At this time, the edge portions of the openings are heat sealed, and the intermediate sheet 23 is joined and integrated with the shape-keeping sheet 24.

The shape-keeping sheet 24 is a fluid-permeable sheet, and its material can be the same as that used for the above-described surface sheet 14 of the base absorbent body 10, for example. The planar shape of the shape-keeping sheet 24 when spread out in a flat sheet form is an approximate rectangle. With spread out and entirely coated with hot-melt adhesive, the shape-keeping sheet 24 is rolled in a cylindrical shape as shown in FIG. 9B, and both of its end sections 24e of the width direction of overlap each other and are joined with the hot-melt adhesive. In this manner, the pulverized-pulp layered body 22, the intermediate sheet 23, and the like are accommodated inside the cylindrical body, from end to end along the longitudinal direction of them.

Also, a front-side portion 24c and a rear-side portion 24d of the longitudinal direction of the shape-keeping sheet 24 shown in FIG. 8 are respectively folded without the pulverized-pulp layered body 22 or the intermediate sheet 23, as shown in FIGS. 9A and 9E. The folded portions 24c and 24d undergo pressure-bonding by embossing with hot-melt adhesive (not shown) being interposed therebetween. As a result, the front-side portion 24c and the rear-side portion 24d of the longitudinal direction of the shape-keeping sheet 24 are sealed so as to become thin sealed sections 25 and 26.

Furthermore, as shown in FIGS. 8 and 9D, in a portion in the rear end section 20b of the top absorbent body 20 where at least the pulverized pulp is present, a leakage-prevention sheet 51 is disposed covering the pulverized-pulp layered body from the back face side. This leakage-prevention sheet 51 is a fluid-impermeable sheet and has a function to prevent liquid absorbed by the pulverized-pulp layered body 22 from seeping to the outer face of the top absorbent body 20. That is, while the sanitary napkin 1 is in use, a case is possible in which the rear end section 20b of the top absorbent body 20 protrudes further backward than a rear edge 10e of the base absorbent body 10, as shown in FIG. 4. In such a case, if liquid seeps to the outer face of the rear end section 20b of the top absorbent body 20, the rear end section 20b soils the undergarment 90 when it touches the undergarment 90; the leakage-prevention sheet 51 prevents such soiling. As a material of the leakage-prevention sheet 51, a nonporous film of polyethylene, polypropylene or the like that can completely block liquid is desirable; however, liquid may not be completely blocked. For example, a nonwoven fabric made up of a water-repellent fiber or the like may be used.

Joining Top Absorbent Body 20 and Base Absorbent Body 10

As shown in FIG. 1, the top absorbent body 20 is superposed on the surface side of the base absorbent body 10, with their center lines CLs of the width direction being matched to each other. That is, the top absorbent body 20 is attached on the base absorbent body 10 at an attachment position so that the center line CL of the width direction of the base absorbent body 10 and that of the top absorbent body 20 are aligned with each other and the front end section 20a of the top absorbent body is superposed on the front end section 10a of the base absorbent body (strictly speaking, the front end section 20a of the top absorbent body protrudes beyond the front end section 10a of the base absorbent body). Note that when the top absorbent body 20 is disposed at the attachment position on the base absorbent body 10, the sealed section 26 at the rear end side of the top absorbent body 20 protrudes backward from the external contour of the base absorbent body 10, to the extent that the user can pinch the sealed section 26 for example. That is, the rear end portion of the rear-side sealed section 26 functions as a pinched section 26a that the user pinches in placing the sanitary napkin.

With the top absorbent body 20 being disposed at the attachment position on the base absorbent body 10, the front end section 20a of the top absorbent body 20 is permanently-joined to the front end section 10a of the base absorbent body 10 firmly. The region that is firmly permanently-joined and shown in dark in FIG. 5 is referred to as a first joined section 10g. In the present embodiment, hot-melt adhesive (indicated as HMA in the figures) is applied to the first joined section 10g (permanently-joined section) of the base absorbent body 10 in a pattern having a plurality of straight lines along the longitudinal direction. The permanent joining is performed by bonding together the portion where the adhesive is applied and the front end section 20a of the top absorbent body 20. The "permanently-joined" condition refers to a condition in which the top absorbent body 20 and the base absorbent body 10 are firmly joined in a non-separable manner to the extent that when separating intentionally the top absorbent body 20 from the base absorbent body 10 is attempted, at least one of them is unavoidably broken. Alternative methods for permanent-joining include channel-embossing, for example. In the present embodiment, as shown in FIG. 2, not only the sealed section 25 of the top absorbent body 20 (length La in the longitudinal direction), but also a portion where the pulverized-pulp layered body 22 is present (length Lg in the longitudinal direction) are permanently-joined. This is because if the portion to be permanently-joined on the top absorbent body 20 is the sealed section 25 only, the rigidity will be insufficient and the top absorbent body 20 will easily move back and forth as a whole.

When the sanitary napkin 1 is not in use, the rear-side sealed section 26 of the top absorbent body 20 and the rear end section 10b of the base absorbent body 10 are temporarily-joined by embossing with the top absorbent body 20 being disposed at the attachment position on the base absorbent body 10. A second joined section 10h, which is a region to be temporarily-joined, is shown in dark in FIG. 1. The "temporarily-joined" condition refers to a condition in which the base absorbent body 10 and the top absorbent body 20 are joined loosely to the extent that the user can easily separate the top absorbent body 20 from the base absorbent body 10 without impairing functions thereof.

Also as shown in FIG. 8, on the back face side of the top absorbent body 20, a fastening member 27 is disposed that is for fastening the rear end section 20b of the top absorbent body 20 to the rear region of the surface sheet 14 of the base absorbent body 10. The fastening member 27 restricts the top absorbent body 20 from moving while the sanitary napkin 1 is in use, and then makes the top absorbent body 20 remain at a suitable position that has been adjusted when the sanitary napkin 1 is placed. In addition, in the sanitary napkin 1 of the present embodiment, while the sanitary napkin 1 is not in use, the top absorbent body 20 and the base absorbent body 10 are temporarily-joined by the fastening section 27, with the top absorbent body 20 being disposed at the attachment position on the base absorbent body 10. That is, the fastening member 27 restricts relative shifting between the base absorbent body 10 and the top absorbent body 20 while the sanitary napkin 1 is not in use. For this reason, the fastening member 27 of the present embodiment is a member that can be re-joined.

As the fastening member 27, an adhesive member or a hook member (a male member of a hook-and-loop fastener) or the like can be used. For example, a hook member in which a plurality of mushroom-shaped pins are arranged, tangling the mushroom-shaped pins in fibers of the surface sheet 14 of the base absorbent body 10 allows the top absorbent body to be fastened to the base absorbent body. Also, as a hook member in which a plurality of needle-shaped pins inclined at a certain angle relative to the flat surface are arranged, there is a hook member, for example, in which when pulled in one direction the hook member is difficult to be hooked to fibers and fastening is easily released, whereas when pulled in the opposite direction the hook member is easily hooked to fibers and fastening is easily achieved. Also, for the purpose of improving the fastening force, a female member of the hook-and-loop fastener that corresponds to the male member of the hook-and-loop fastener disposed on the side of the top absorbent body 20 may be disposed in the base absorbent body 10. The male member may be disposed in the base absorbent body 10, and further the female member may be disposed in the top absorbent body 20.

Wrapping of Sanitary Napkin 1

Next, a method for wrapping the sanitary napkin 1 will be described. FIG. 10 shows explanatory diagrams illustrating a procedure in which the sanitary napkin 1 to be wrapped is folded. FIG. 10A shows the sanitary napkin 1 before it is folded, FIG. 10B shows the sanitary napkin 1 that is being bent at a first folding position, FIG. 10C shows the sanitary napkin 1 that is being bent at a second folding position, and FIG. 10D shows the sanitary napkin 1 that is being bent at a third folding position.

In the sanitary napkin 1, the holding sections 32 are bent in towards the top absorbent body 20, and protection sheets 35 are disposed that cover adhesive 33 on the back face side of the holding sections 32 on both sides. The sanitary napkin 1 including the protection sheets 35 is folded, while being conveyed, at three positions of the longitudinal direction together with a rectangular-shaped wrapping sheet 36 that is disposed on the back face side. At this time, the base absorbent body 10 and the top absorbent body 20 are superposed, and bent towards the surface side such that the top absorbent body 20 is placed inside.

Incidentally, the holding sections 32 and the protection sheets 35 bond together such that the face of each protection sheet 35 on which the adhesive 33 and a release agent are applied faces the back face of each holding section 32 before being folded inwards. Thereafter, the holding sections 32 that have been attached to the protection sheets 35 are folded in towards the top absorbent body 20, and the two protection sheets 35 are joined and integrated at the overlapping portion thereof in the center of the width direction with adhesive that has been applied in advance. After that, onto the face of the joined-and-integrated protection sheets 35 opposite to the face to which the release agent is applied, only adhesive is applied. The adhesive on the protection sheets 35 and the rear end section of the wrapping sheet 36 are superposed when the sanitary napkin 1 is folded. As a result thereof, when the user unwraps the sanitary napkin 1, the adhesive 33 adheres and remains on the holding sections 32 due to action of the release agent; then, the shift-prevention attaching sections 33 are formed in the holding sections 32.

When the sanitary napkin 1 and the wrapping sheet 36 are folded, they are conveyed on a conveyor table (not shown), placed such that the longitudinal direction thereof intersects the direction of conveyance. The sanitary napkin 1 and the wrapping sheet 36 that are being conveyed are held, at the first folding position, between the conveyor table and a first disk 60 that rotates about a shaft parallel to the direction intersecting the direction of conveyance; the sanitary napkin 1 and the wrapping sheet 36 are bent upward from the first folding position by a guide member (not shown), the guide member being disposed closer to the rear end of the sanitary napkin 1 than the first disk 60. The guide member is such that the bend angle is increased forward away from a portion near the first disk 60 in the direction of conveyance. Therefore the sanitary napkin 1 and the wrapping sheet 36 are folded by being gradually bent upward at the increasing bend angle during conveyance.

The sanitary napkin 1 and the wrapping sheet 36 folded at the first folding position are conveyed to the position where a second disk 61 is disposed adjusted to the second folding position. Then, the sanitary napkin 1 and the wrapping sheet 36 are held between the conveyor table and the second disk 61 and bent upward from the second folding position by a guide member (not shown), the guide member being disposed relative to the second disk 61 on the side which of the sanitary napkin 1 has already been folded. The guide member is such that the bend angle is increased forward away from a portion near the second disk 61 in the direction of conveyance. Therefore the sanitary napkin 1 and the wrapping sheet 36 are folded by being gradually bent upward at the increasing angle during conveyance.

The sanitary napkin 1 and the wrapping sheet 36 folded at the second folding position are conveyed to the position where a third disk 62 is disposed adjusted to the third folding position. Then, the sanitary napkin 1 and the wrapping sheet 36 are held between the conveyor table and the third disk 62 and bent upward from the third folding position by a guide member (not shown), the guide member disposed on the front end side of the sanitary napkin relative to the third disk 62. The guide member is such that the bend angle is increased forward away from a portion near the third disk 62 in the direction of conveyance. Therefore the sanitary napkin 1 and the wrapping sheet 36 are folded by being gradually bent upward at the increasing angle during conveyance.

In this manner, the sanitary napkin 1 is folded through three folding steps, and results in being wrapped with the wrapping sheet 36. A piece of tape 38 disposed in the front side of the wrapping sheet 36 is attached to the outer face of the wrapping sheet 36. Bonding of an edge section 36c of the longitudinal direction of the wrapping sheet 36 folded with the sanitary napkin 1 is performed during folding, and the sanitary napkin 1 is supplied to users.

Note that as shown in the cross-sectional view in FIG. 2, at three positions P1, P2 and P3 in the longitudinal direction, there are portions extending over the entire region in the width direction having the smaller basis weight of the pulverized pulp than other portions in the longitudinal direction. These portions are for making it easy to fold the sanitary napkin 1 in four in a wrapping process, which is to be described later. That is, the positions P1, P2 and P3 in the longitudinal direction respectively correspond to folding positions for wrapping. The folding position P1 on the rear end section side is referred to as a first folding position P1, the folding position P3 on the front end section side is referred to as a third folding position P3, and the folding position P2 near the middle between these positions is referred to as a second folding position P2.

Wearing Sanitary Napkin 1 on Human Body

The sanitary napkin 1 is in the above-described wrapped condition when supplied to a user, and the wrapping sheet 36 thereof is unsealed by the user removing the tape 38. At the same stage, the protection sheets 34 and 35 are removed so that the shift-prevention attaching sections 31 of the back face of the back face sheet 30 and the shift-prevention attaching sections 33 of the back face of the holding sections 32 are exposed.

The unwrapped sanitary napkin 1 is disposed at an any position on the undergarment 90 as shown in FIG. 4, and attached and fixed to the inner face of the undergarment 90 with the shift-prevention attaching sections 31. At this stage, the holding sections 32 are folded back towards the undergarment 90 and attached and fixed to the outer face of the undergarment 90 with the shift-prevention attaching sections 33. After pulling up the undergarment to which the sanitary napkin 1 has been fixed towards the human body, the user pinches the pinched section 26a to pull up the top absorbent body 20. Consequently, the temporary-joining between the base absorbent body 10 and the top absorbent body 20 is released, and the rear end section 20b side of the top absorbent body 20 is separated from the base absorbent body 10.

Thereafter, by the user moving the pinched section 26a in the longitudinal direction, the position of the top absorbent body 20 is adjusted such that the top absorbent body 20 fits into a groove such as the buttocks of the human body and comes into close contact with the human body. In the condition in which the position of the top absorbent body 20 is adjusted, the fastening member 27 of the top absorbent body 20 is fastened and fixed to the base absorbent body 10 or the inner face of the undergarment 90 as shown in FIG. 4; or depending on the shape of a user, the fastening member 27 may be fastened to the undergarment 90, extending beyond the base absorbent body 10. In this manner the top absorbent body 20 is positioned in proper contact with the human body.

Folding Positions and Restricting Members

Figure 11A:
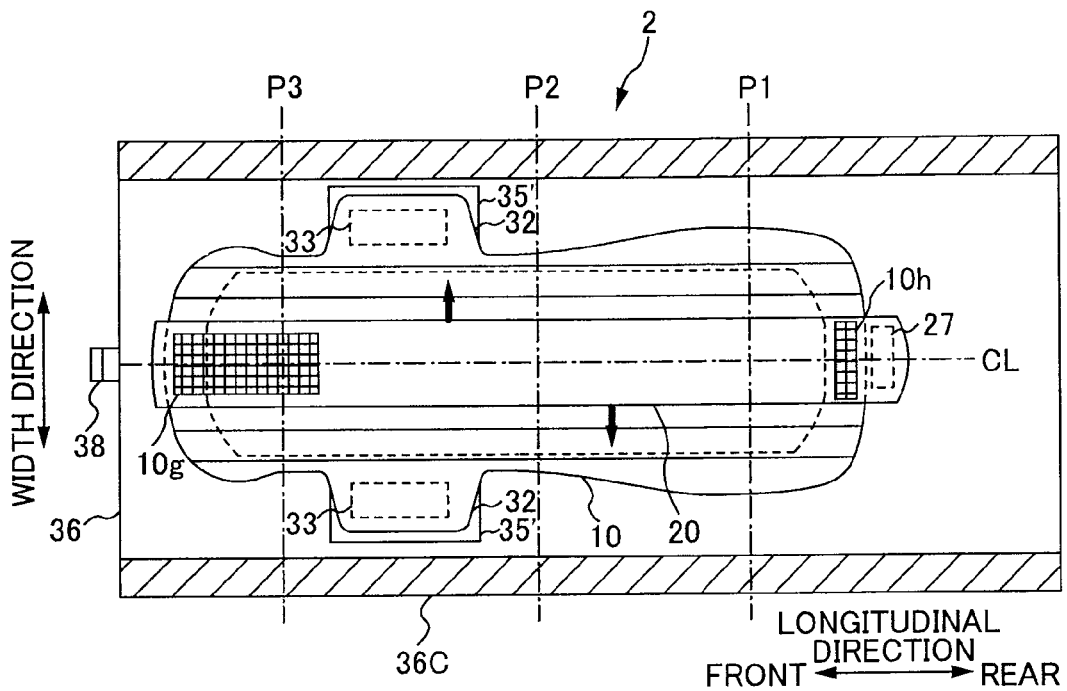
[FIG. 11A] This is a diagram showing the state of a sanitary napkin of a comparative example, which is different from the embodiments of the invention, immediately before being folded.
Figure 11B:
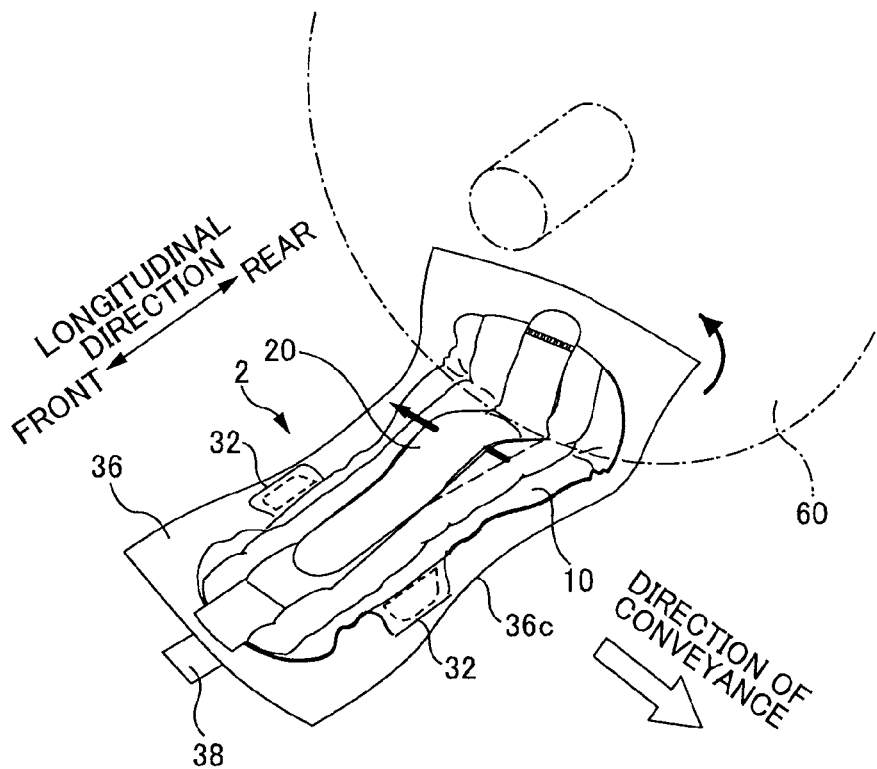
[FIG. 11B] This is a diagram showing how the sanitary napkin of the comparative example is folded at a first folding position.

FIG. 11A is a diagram showing a state of a sanitary napkin 2 of a comparative example, which is different from the present embodiments, immediately before being folded. FIG. 11B is a diagram showing how the sanitary napkin 2 of the comparative example is folded at the first folding position P1. In the sanitary napkin 2 of the comparative example, the fastening member 27 is disposed on the back face side of the top absorbent body 20 further closer to the rear end than a second joined section 10h (portion indicated by a lattice pattern in FIG. 11A). Specifically, in the above-described sanitary napkin 1 of the present embodiment, the base absorbent body 10 and the top absorbent body 20 are temporarily joined by the fastening member 27 while not in use, whereas in the sanitary napkin 2 of the comparative example, while not in use, the top absorbent body 20 and the base absorbent body 10 are not temporarily joined by the fastening member 27 between the first joined section 10g (portion indicated by a lattice pattern in FIG. 11A) and the second joined section 10h.

Also, when the above-described sanitary napkin 1 of the present embodiment is folded, the holding sections 32 are folded in towards the top absorbent body 20, and the top absorbent body 20 is sandwiched between the base absorbent body 10 and the protection sheets 35 bonding with the top faces of the holding sections 32 that have been folded back (FIG. 10). On the other hand, when the sanitary napkin 2 of the comparative example is folded, the holding sections 32 are left open, instead of being folded in towards the top absorbent body 20. Note that in the sanitary napkin 2 of the comparative example, protection sheets 35' are disposed on the back face of the opened holding sections 32 with the adhesive 33.

Also, in the front end side of the sanitary napkin 2 of the comparative example, the first joined section 10g is present on which the top absorbent body 20 and the base absorbent body 10 are permanently joined, in the same manner as in the sanitary napkin 1 of the present embodiment; in the rear end side, the second joined section 10h is present on which the top absorbent body 20 and the base absorbent body 10 are temporarily joined. That is, unless more force is applied than is required to release the temporary-joining between the top absorbent body 20 and the base absorbent body 10, the top absorbent body 20 does not shift from the attachment position on the base absorbent body 10, on the first joined section 10g and the second joined section 10h. In contrast, between the first joined section 10g and the second joined section 10h, there is no portion that restricts relative shifting between the top absorbent body 20 and the base absorbent body 10. Therefore, the top absorbent body 20 easily shifts from the attachment position on the base absorbent body 10.

Specifically, when the sanitary napkin 2 of the comparative example is folded for individual wrapping, there is a possibility that the top absorbent body 20 and the base absorbent body 10 will move relatively so that the top absorbent body 20 will shift from the attachment position on the base absorbent body 10. Especially, as shown in FIGS. 10B and 11B, since the sanitary napkins of the present embodiment and the comparative example are folded while being held between the conveyor table (not shown) and the first disk 60 at the first folding position P1, the possibility increases that the conveyance operation of the sanitary napkin is inhibited by the disk so that the top absorbent body 20 shifts from the attachment position on the base absorbent body 10. Suppose that the base absorbent body 10 is conveyed while being sucked to the conveyor table, for example. The base absorbent body 10 is not likely to be affected by the disk; however the top absorbent body 20 is likely to be affected by the disk. Therefore, it is considered that the top absorbent body 20 shifts relative to the base absorbent body 10 in the width direction corresponding to the direction of conveyance, and that when the sanitary napkin 2 enters a small gap between the conveyor table and the disk the top absorbent body 20 contacts the disk so that the sanitary napkin 2 is pushed in the opposite direction to the direction of conveyance.

Figure 11C:
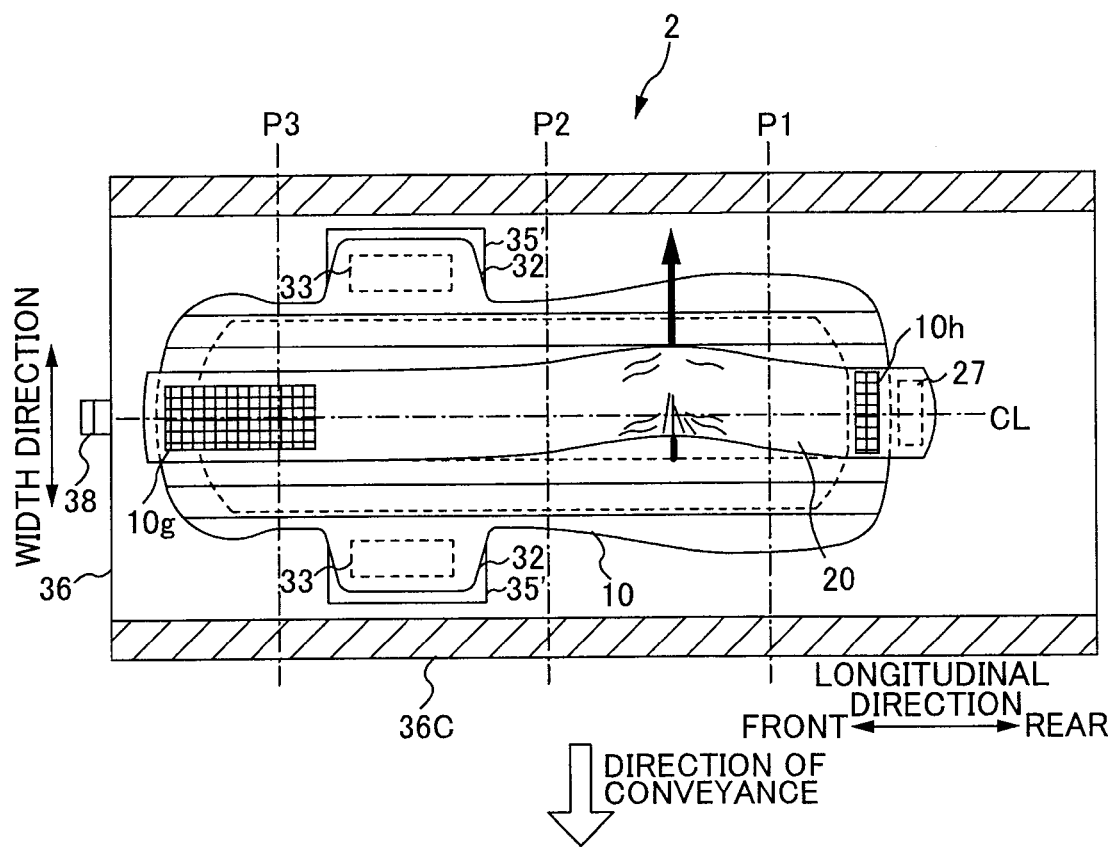
[FIG. 11C] This is a diagram showing the unwrapped state of a sanitary napkin of a comparative example that had been folded with the top absorbent body being shifted relative to the base absorbent body.

FIG. 11C is a diagram showing the unwrapped state of the sanitary napkin 2 of a comparative example that has been folded with the top absorbent body 20 being shifted relative to the base absorbent body 10. As shown in the figure, if the top absorbent body 20 is folded with being shifted from the attachment position on the base absorbent body 10, the surface sheet 14 of the top absorbent body 20 wrinkles irregularly. In that case, a gap will occur between the absorbent-body base material 12 and the surface sheet 14 in contact with the human body, and liquid may leak from that gap. Also, if the top absorbent body 20 wrinkles irregularly, or if the sanitary napkin 2 is folded without the sides of the longitudinal direction of the top absorbent body 20 being aligned to the sides of the longitudinal direction of the base absorbent body 10, the napkin does not have a good appearance when the user unwraps and takes out the sanitary napkin 2, and therefore cannot give the user a good impression of the product.

Therefore, an object of the present embodiment is to provide a sanitary napkin capable of preventing the top absorbent body 20 from relatively shifting from the base absorbent body 10 when the sanitary napkin is folded. In the present embodiment, restricting members are disposed between the first joined section 10g and the second joined section 10h so that the relative shifting between the top absorbent body 20 and the base absorbent body 10 is prevented while the sanitary napkin is folded.

Figure 12A:
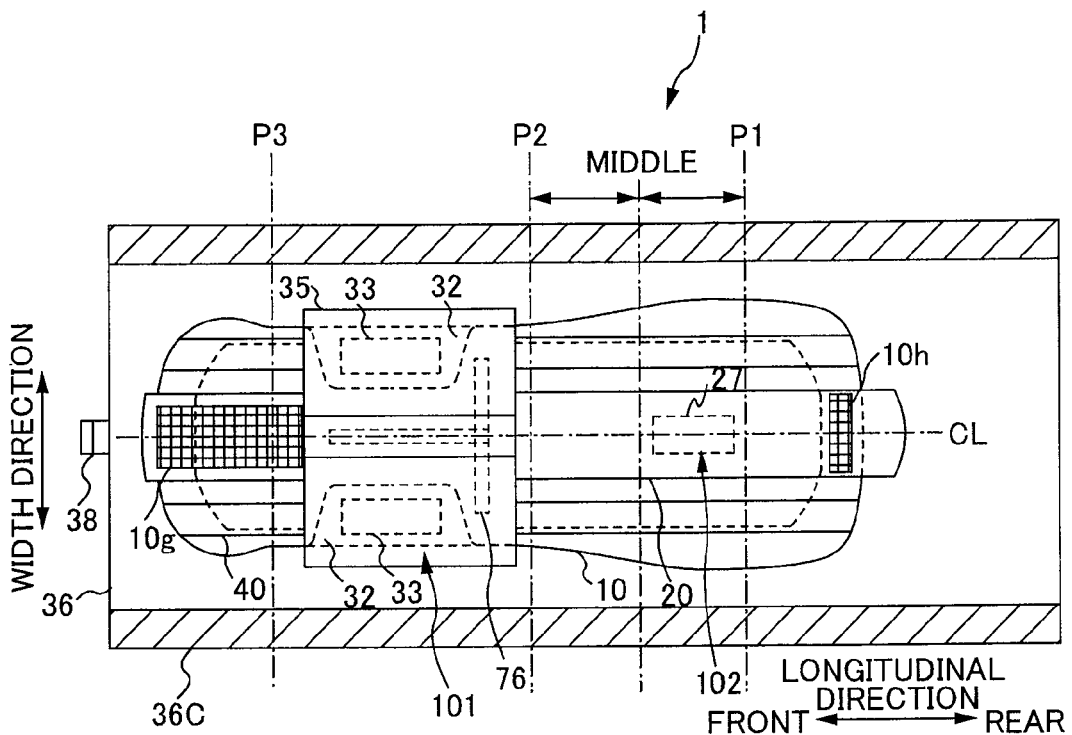
[FIG. 12A] This is a diagram showing the state of the sanitary napkin of the present embodiment immediately before being folded.

FIG. 12A shows a state of the sanitary napkin 1 of the present embodiment immediately before being folded. The holding sections 32 are folded in towards the top absorbent body 20, and the top face of the folded holding sections 32 and the protection sheets 35 bond together. The fastening member 27 is disposed between the holding sections 32 and the second joined section 10h, closer to the first folding position P1 than the middle between the first folding position P1 and the second folding position P2. Note that the first folding position P1 does not overlap with the fastening member 27.

In the area between the first joined section 10g and the second joined section 10h, the top absorbent body 20 is held between the base absorbent body 10 and the protection sheets 35 bonding with the top face of the folded holding sections 32; this makes it possible to restrict the relative shifting between the top absorbent body 20 and the base absorbent body 10 when the sanitary napkin 1 is folded. That is, when a portion where the top absorbent body 20 is sandwiched between the base absorbent body 10 and the protection sheets 35 bonding with the top face of the folded holding sections 32 (corresponding to the portions of the sheets and the main body section between which an absorbent body is sandwiched) is defined as a holding restricting section 101, the holding restricting section 101 functions as a restricting member that restricts relative shifting between the top absorbent body 20 and the base absorbent body 10 when the sanitary napkin 1 is folded.

Also, in the area between the first joined section 10g and the second joined section 10h, the top absorbent body 20 and the base absorbent body 10 are temporarily joined by the fastening member 27 that is disposed on the back face side of the top absorbent body 20 so as to oppose the base absorbent body 10; this makes it possible to restrict the relative shifting between the top absorbent body 20 and the base absorbent body 10 when the sanitary napkin 1 is folded. That is, when a portion where the top absorbent body 20 and the base absorbent body 10 are temporarily joined by the fastening member 27 is defined as a temporary-joining restricting section 102, the temporary-joining restricting section 102 functions as a restricting member that restricts relative shifting between the top absorbent body 20 and the base absorbent body 10 when the sanitary napkin is folded.

In this way, in the sanitary napkin 1 of the present embodiment, since the holding restricting section 101 and the temporary-joining restricting section 102 are disposed between the first joined section 10g and the second joined section 10h, it is possible to prevent relative shifting between the top absorbent body 20 and the base absorbent body 10 when the sanitary napkin 1 is folded.

Next, functions of each restricting member at each folding position will be described. The sanitary napkin 1 of the present embodiment is folded together with the wrapping sheet 36 while conveyed at three positions of the longitudinal direction, in the following order: the first folding position P1 which is the closest to the rear end side, the second folding position P2, and the third folding position P3.

Between the first folding position P1 and the first joined section 10g, the relative shifting between the top absorbent body 20 and the base absorbent body 10 is restricted by the holding restricting section 101 and the temporary-joining restricting section 102. Therefore, the sanitary napkin 1 is folded without the top absorbent body 20 shifting from the attachment position on the base absorbent body 10. In contrast, between the first folding position P1 and the second joined section 10h, neither the holding restricting section 101 nor the temporary-joining restricting section 102 is disposed. However, in the sanitary napkin 1 of the present embodiment, since the interval between the first folding position P1 and the second joined section 10h is comparatively small, it is possible to restrict the relative shifting between the top absorbent body 20 and the base absorbent body 10 only with the second joined section 10h, without providing a restricting member. As a result, the sanitary napkin 1 is folded without the top absorbent body 20 shifting from the attachment position on the base absorbent body 10.

Also, since the sanitary napkin 1 is held between the disk and the conveyor table at the folding position, the top absorbent body 20 is more likely to shift from the attachment position at the folding position and the vicinity thereof. For this reason, for example, when the sanitary napkin 1 is folded at the first folding position P1, it is important that relative shifting between the top absorbent body 20 and the base absorbent body 10 is restricted by the temporary-joining restricting section 102, which is closer to the first folding position P1 than the holding restricting section 101. The closer the temporary-joining restricting section 102 is to the first folding position P1, the more reliably relative shifting between the top absorbent body 20 and the base absorbent body 10 can be restricted. Accordingly, in the present embodiment, the fastening member 27 is disposed closer to the first folding position P1 than the middle between the first folding position P1 and the second folding position P2, and such a fastening member 27 serves as the temporary-joining restricting section 102.

However, the fastening member 27 is disposed at a position that does not overlap with the first folding position P1. The reason is as follows. Since the fastening member 27 is formed of a member having a high rigidity such as a hook member or adhesive, it will be difficult to fold the sanitary napkin 1 if the first folding position P1 overlaps with the fastening member 27.

Figure 12B:
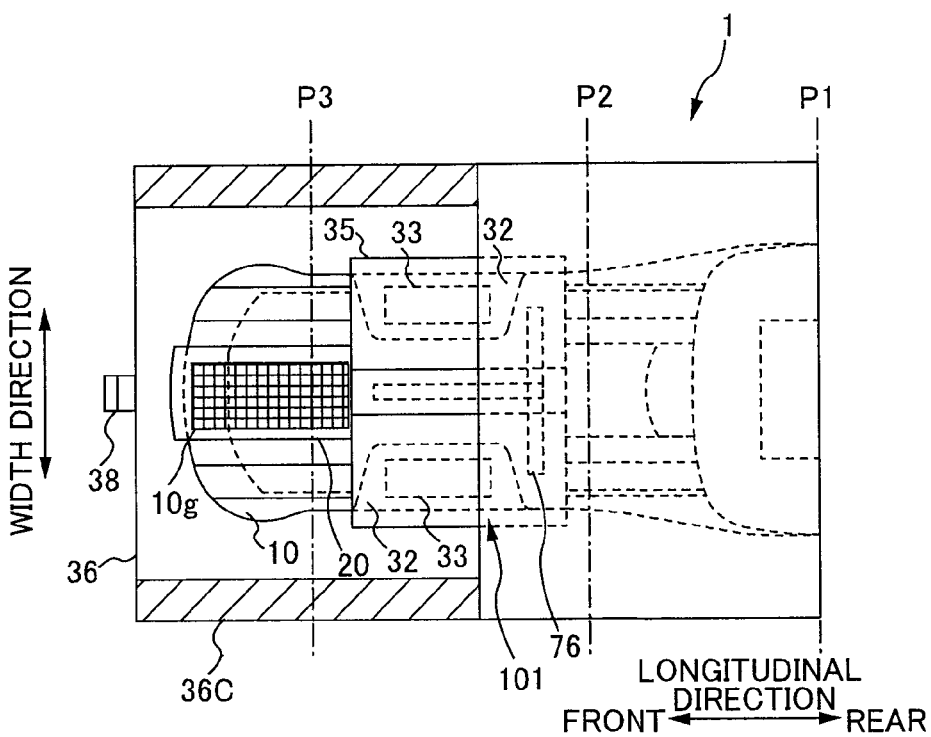
[FIG. 12B] This is a diagram showing the state of the sanitary napkin that is folded once at the first folding position.

FIG. 12B shows the state of a sanitary napkin that is folded once at the first folding position P1. After being folded at the first folding position P1, the sanitary napkin is folded at the second folding position P2. Between the second folding position P2 and the first joined section 10g, relative shifting between the top absorbent body 20 and the base absorbent body 10 is restricted by the holding restricting section 101. Therefore, the sanitary napkin is folded without the top absorbent body 20 shifting from the attachment position on the base absorbent body 10.

In contrast, on the side close to the rear end with respect to the second folding position P2, the temporary-joining restricting section 102 (not shown) restricts the relative shifting between the top absorbent body 20 and the base absorbent body 10. In addition, the wrapping sheet 36 folded at the first folding position P1 bonds with the protection sheets 35 with adhesive 76, and consequently the portions of the top absorbent body 20 and the base absorbent body 10 that are superposed by folding at the first folding position P1 is wrapped by the wrapping sheet 36. That is, on the side close to the rear end with respect to the second folding position P2, the relative shifting between the top absorbent body 20 and the base absorbent body 10 is restricted not only by the temporary-joining restricting section 102, but also by superposing the portion close to the rear end with respect to the first folding position P1 and the portion close to the front end with respect to the first folding position P1 in FIG. 12A by folding.

For this reason, it is more important for the temporary-joining restricting section 102 to restrict the relative shifting between the top absorbent body 20 and the base absorbent body 10 when folded at the first folding position P1 (corresponding to the end-section folding position) than when folded at the second folding position P2 (corresponding to the middle folding position). Accordingly, as described above, the temporary-joining restricting section 102 is disposed closer to the first folding position P1 than the middle between the first folding position P1 and the second folding position P2.

Figure 12C:
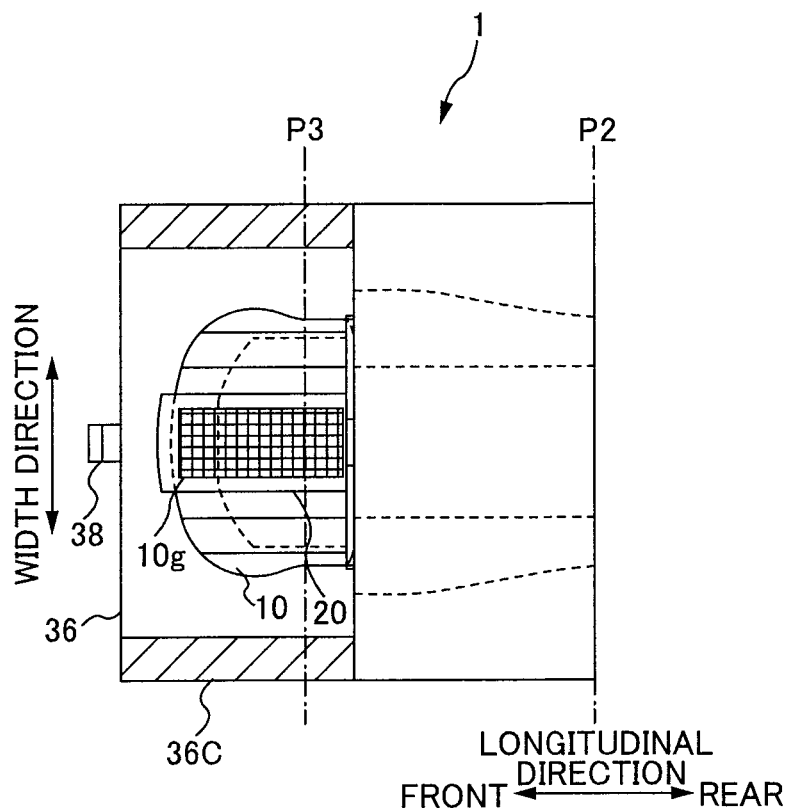
[FIG. 12C] This is a diagram showing the state of the sanitary napkin that is folded at a second folding position.
Figure 12D:
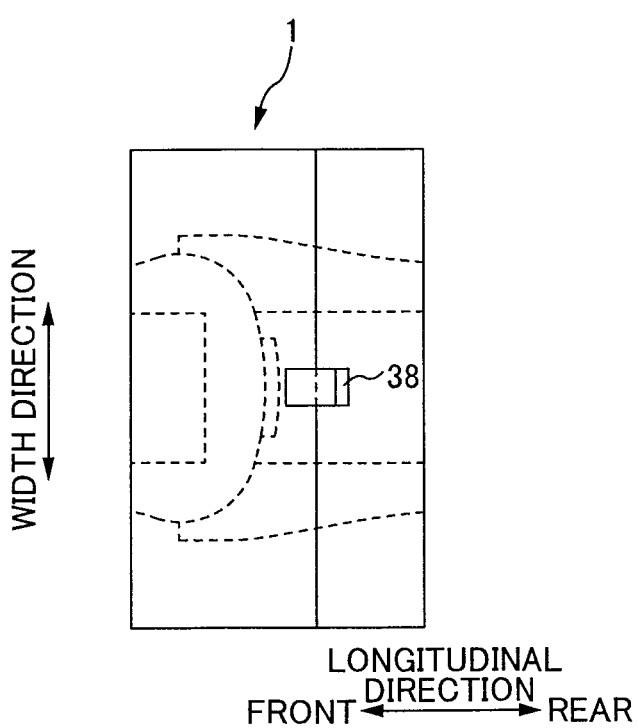
[FIG. 12D] This is a diagram showing the state of the sanitary napkin that is folded at a third folding position and whose individual wrapping has ended.

FIG. 12C shows the state of the sanitary napkin that is folded at the second folding position P2. FIG. 12D shows the state of the sanitary napkin that is folded at the third folding position P3 and whose individual wrapping has ended. As shown in FIG. 12C, on the side close to the front end with respect to the third folding position P3, the base absorbent body 10 and the top absorbent body 20 are permanently joined, serving as the first joined section 10g. Therefore, the top absorbent body 20 does not shift from the attachment position on the base absorbent body 10 when the sanitary napkin is folded. Also, on the side close to the rear end with respect to the third folding position P3, the top absorbent body 20 and the base absorbent body 10 are folded and superposed without relative shifting from each other after the two folding processes. In this manner, the top absorbent body 20 is folded without shifting from the attachment position on the base absorbent body 10. After being folded at the third folding position P3 the top absorbent body 20 is fixed with the tape 38, and individual wrapping of the sanitary napkin 1 ends.

In the present embodiment, a conclusion is as follow: the end sections of the longitudinal direction of the top absorbent body 20 and the base absorbent body 10 are joined at the first joined section 10g; the other end sections thereof are joined at the second joined section 10h; and the restricting members are disposed between the first joined section 10g and the second joined section 10h, the restricting members restricting the relative shifting between the top absorbent body 20 and the base absorbent body 10 when the top absorbent body 20 and the base absorbent body 10 that are superposed are folded.

As a result, it is possible to prevent the relative shifting between the top absorbent body 20 and the base absorbent body 10 when the sanitary napkin 1 is folded. That is, the top absorbent body 20 can be folded without shifting from the attachment position on the base absorbent body 10, and the sanitary napkin 1 can be provided that is folded with the center lines CL of the width direction of the top absorbent body 20 and the base absorbent body 10 being aligned.

Note that the holding sections 32 are used to fix the undergarment 90 and the fastening member 27 is used to fix the position of the top absorbent body 20 while the sanitary napkin 1 is worn. In other words, it is possible to cause the holding sections 32 and the fastening member 27 which perform functions other than that of the restricting member to serve as the restricting member or apart of the restricting member, without including another restricting member that restricts movement of the top absorbent body 20 and the base absorbent body 10 between the first joined section 10g and the second joined section 10h.

SANITARY NAPKIN 3 OF FIRST MODIFIED EXAMPLE

Figure 13:
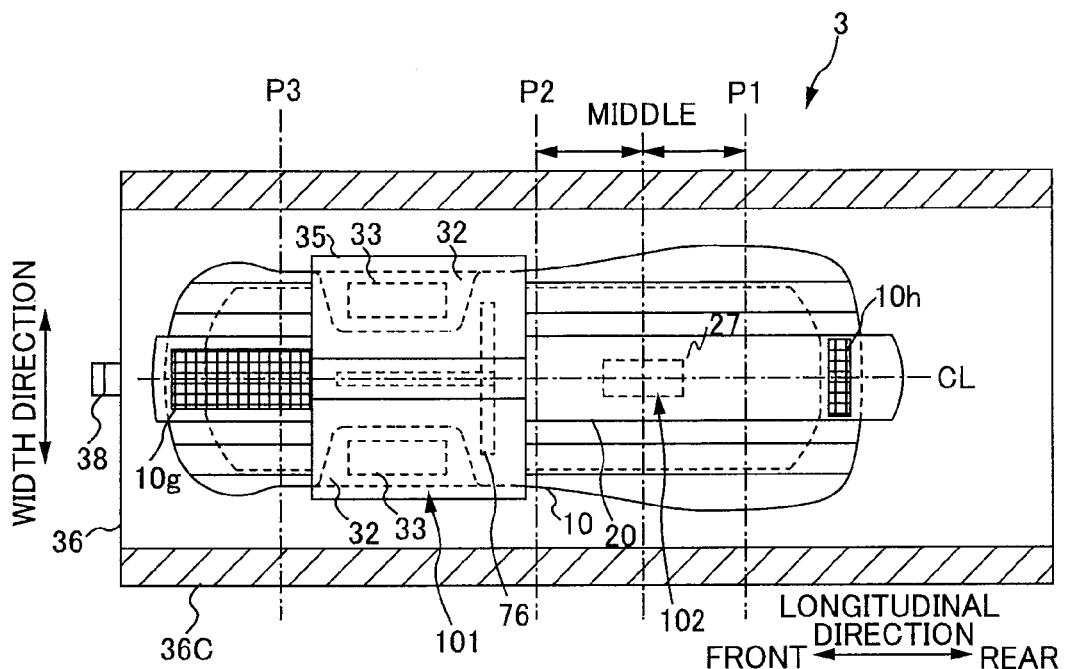
[FIG. 13] This is a diagram showing a sanitary napkin of the first modified example.

FIG. 13 shows a sanitary napkin 3 of the first modified example. In the foregoing embodiment, as shown in FIG. 12A, the temporary-joining restricting section 102 (fastening member 27) is disposed closer to the first folding position P1 than the middle between the first folding position P1 and the second folding position P2. However, there is no limitation to this, and the fastening member 27 may be disposed at any position as long as such a position is located between the first joined section 10g and the second joined section 10h. For example, as in the sanitary napkin 3 of the first modified example shown in FIG. 13, the temporary-joining restricting section 102 (fastening member 27) may be disposed in the middle between the first folding position P1 and the second folding position P2. In such a case, restricting the relative shifting between the top absorbent body 20 and the base absorbent body 10 when the sanitary napkin 3 is folded at the first folding position P1 has the same effect as when the sanitary napkin 3 is folded the second folding position P2.

In addition, if it is desired to restrict better the relative shifting between the top absorbent body 20 and the base absorbent body 10 in the vicinity of the second folding position P2, the temporary-joining restricting section 102 (fastening member 27) can be disposed closer to the second folding position P2 than the middle between the first folding position P1 and the second folding position P2.

Also in the foregoing embodiment, since a member having a high rigidity is used for the fastening member 27, the temporary-joining restricting section 102 does not overlap with the folding position. However, there is no limitation to this. For example, the temporary-joining restricting section 102 may overlap with the folding position if a member having a low rigidity is used for the fastening member 27 and the top absorbent body 20 and the base absorbent body 10 are temporarily joined such that they are re-joinable. The top absorbent body and the base absorbent body 10 are most likely to shift from each other at the folding position. Therefore, providing the restricting member at the folding position makes it possible to restrict better the relative shifting between the top absorbent body 20 and the base absorbent body 10. Also, if the member having a low rigidity overlaps with the folding position, this does not make it difficult to fold the sanitary napkin.

SANITARY NAPKIN 4 OF SECOND MODIFIED EXAMPLE

Figure 14A:
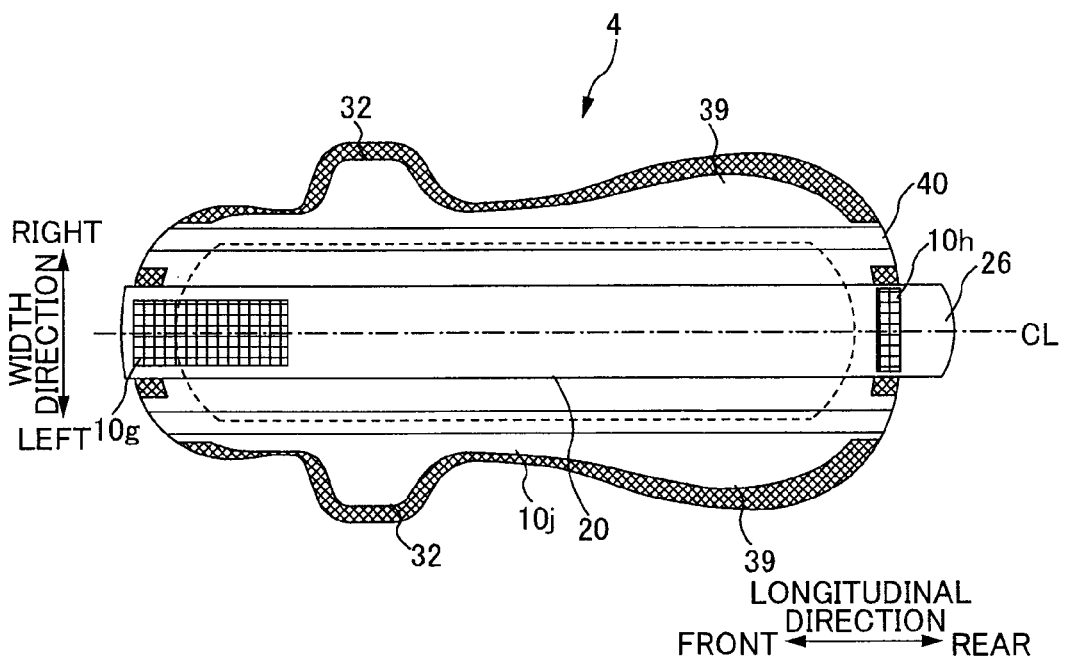
[FIG. 14A] This is a diagram showing the surface side of a sanitary napkin of the second modified example.
Figure 14B:
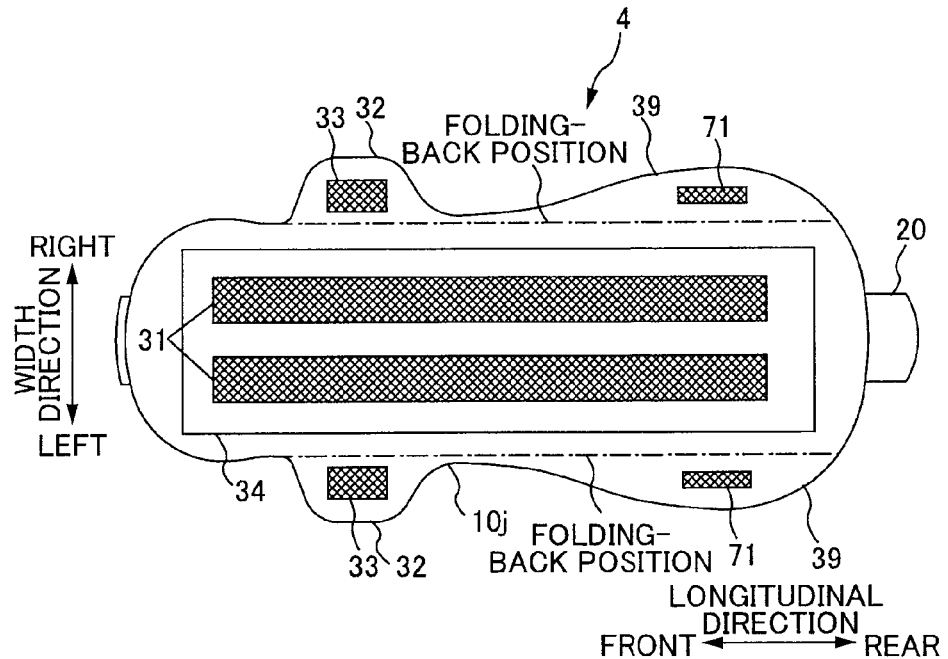
[FIG. 14B] This is a diagram showing the back face side of the sanitary napkin of the second modified example.

FIG. 14A shows the surface side of a sanitary napkin 4 of the second modified example. FIG. 14B shows the back face side of the sanitary napkin 4 of the second modified example. Compared with the above-described sanitary napkin 1 shown in FIG. 1, a base absorbent body 10j of the sanitary napkin 4 of the second modified example starts gradually becoming wider in the width direction from around the holding sections 32 towards the rear end. The portions in the rear side of the base absorbent body 10j that extend further in the width direction are referred to as rear holding sections 39. The rear holding sections 39 can receive liquid that is going to flow out of the sides of the rear portions of the top absorbent body 20 and the base absorbent body 10j.

Since the rear holding sections 39 protrude in the width direction relative to the side sheets 40, similarly to the holding sections 32, the rear holding sections 39 are folded in towards the top absorbent body 20 when individually wrapped. The dot-dash line extending the longitudinal direction shown in FIG. 14B is the folding-back position when the holding sections 32 and the rear holding sections 39 are folded in towards the top absorbent body 20. Also, on the back face side of the rear holding sections 39, "shift-prevention attaching sections 71" are formed. The shift-prevention attaching sections 71, together with the shift-prevention attaching sections 31, cause the sanitary napkin 4 to be attached and fixed to the inner face of the undergarment 90.

Figure 14C:
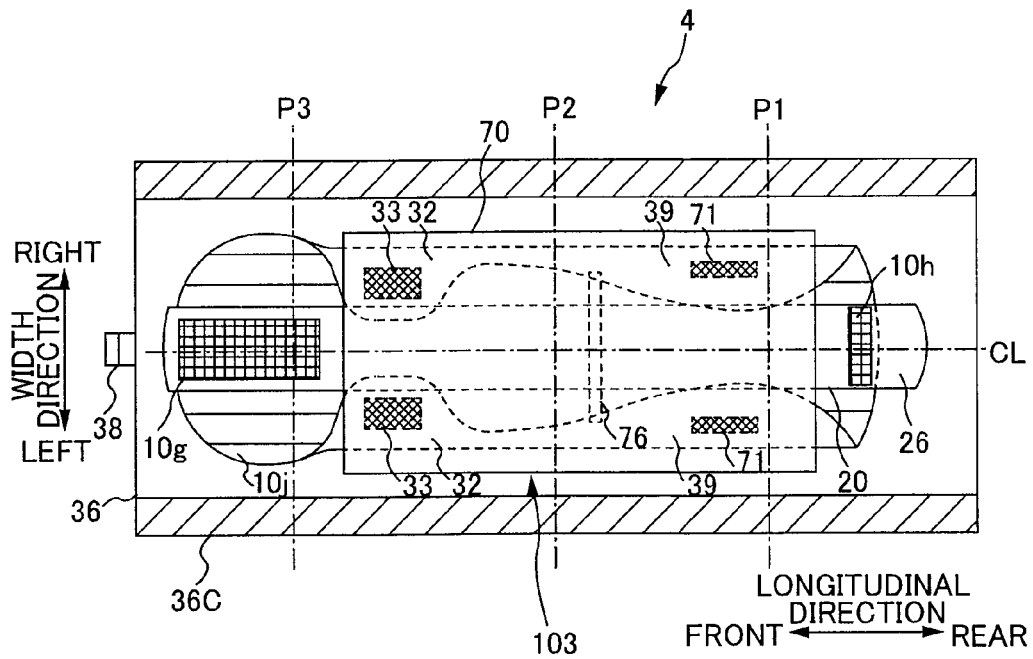
[FIG. 14C] This is a diagram showing the sanitary napkin of the second modified example whose holding sections and rear holding sections are folded in towards the top absorbent body.

FIG. 14C shows of the sanitary napkin 4 of the second modified example whose holding sections 32 and rear holding sections 39 are folded in towards the top absorbent body 20. On the top faces of the folded holding sections 32 and the rear holding sections 39, a single protection sheet 70 is attached with adhesives 33 and 71. Accordingly, the top absorbent body 20 between the first joined section 10g and the second joined section 10h is held between the base absorbent body 10j and the single protection sheet 70. This makes it possible to prevent the relative shifting between the top absorbent body 20 and the base absorbent body 10j when the sanitary napkin 4 is folded. That is, in the sanitary napkin 4 of the second modified example, when a portion where the top absorbent body 20 is sandwiched between the base absorbent body 10j and the single protection sheet 70 bonding with the top faces of the folded holding sections 32 and rear holding sections 39 is defined as a holding restricting section 103, the holding restricting section 103 functions as a restricting member.

In the sanitary napkin 4 of the second modified example, the region between the first joined section 10g and the second joined section 10h serves as the holding restricting section 103 for the most part. Also, the first folding position P1 and the second folding position P2 are positioned on the protection sheet 70. In other words, the folding positions where the relatively shifting between the top absorbent body 20 and the base absorbent body 10j are most likely to happen are on the holding restricting section 103, and therefore it is possible to reliably prevent the top absorbent body 20 from shifting from the attachment position on the base absorbent body 10j.

Also, when the above-described sanitary napkin 1 and the wrapping sheet 36 (FIG. 12B) are folded at the second folding position P2, the superposed top absorbent body 20 and base absorbent body 10j are wrapped by the wrapping sheet 36. Therefore, the relative shifting between the top absorbent body 20 and the base absorbent body 10 at the second folding position is reliably restricted. However, when the rear side of the wrapping sheet 36 is short relative to the sanitary napkin 4 as shown in FIG. 14C, the folded wrapping sheet 36 does not cover the second folding position (therefore, the adhesive 76 for the protection sheet 70 and the wrapping sheet 36 is applied close to the rear end with respect to the second folding position P2). In such a case, as in the sanitary napkin 4 of the second modified example, setting the second folding position P2 on the single protection sheet 70 that is long in the longitudinal direction makes it possible to restrict the relative shifting between the top absorbent body 20 and the base absorbent body 10 at the folding position.

In addition, in the above-described sanitary napkin 1, as shown in FIG. 12A, the temporary-joining restricting section 102 (fastening member 27) is disposed between the holding restricting section 101 and the second joined section 10h. In the sanitary napkin 4 of the second modified example, the holding restricting section 103 extends to the vicinity of the second joined section 10h, and therefore the temporary-joining restricting section (fastening member 27) need not be disposed between the first joined section 10g and the second joined section 10h. For example, the fastening member 27 may be disposed at the sealed section 26, which is the rear end section of the top absorbent body 20. Then, by temporarily joining the top absorbent body 20 and the base absorbent body 10j with the fastening member 27, the second joined section 10h may be formed. In such a case, the following method for keeping the position of the top absorbent body 20 steady with the fastening section 27 is also possible: after the user places the sanitary napkin in the undergarment 90 and has adjusted the position of the top absorbent body 20, the user folds the rear end of the top absorbent body 20 towards the skin side surface of the back face of the undergarment 90 or on the edge of the undergarment 90.

Figure 15A:
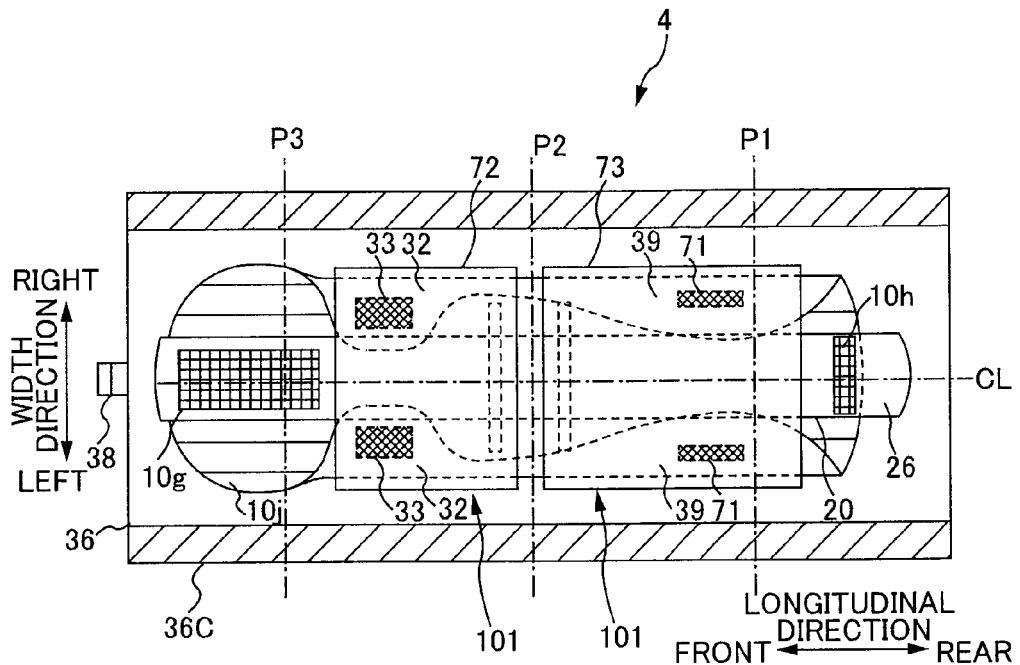
[FIG. 15A] This is a reference example of a protection sheet of the second modified example.
Figure 15B:
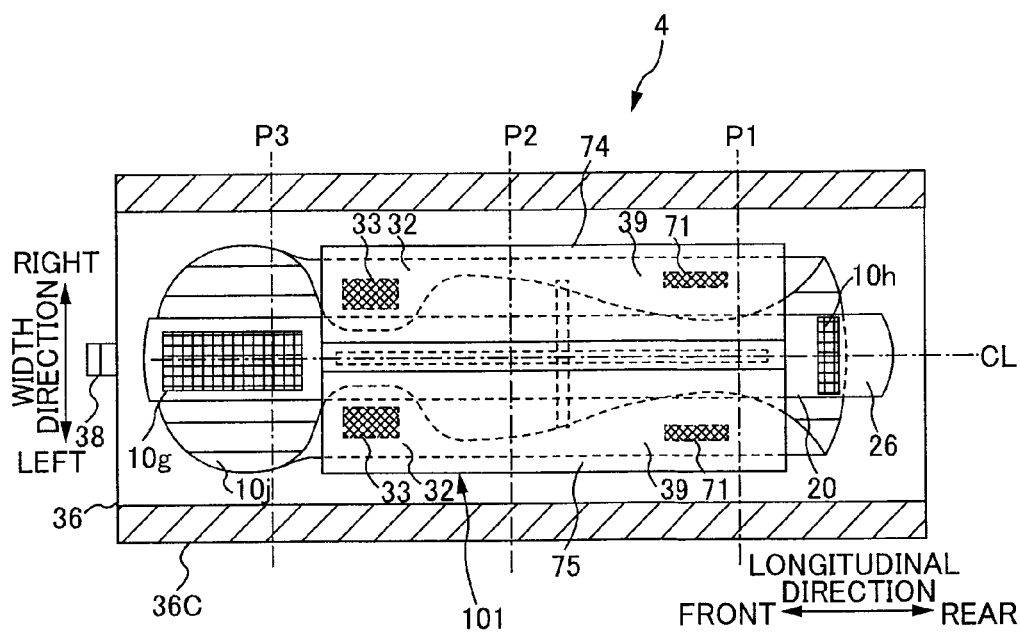
[FIG. 15B] This is a reference example of the protection sheet of the second modified example.

Note that the number of the protection sheets disposed on the top face of the folded holding sections 32 and the rear holding sections 39 is not limited to one. FIGS. 15A and 15B are reference examples of a method for arranging a protection sheet in the sanitary napkin 4 of the second modified example. For example, as shown in FIG. 15A, the protection sheets 72 and 73 may be disposed for each of a set of the holding sections 32 and a set of the rear holding sections 39, and two holding restricting sections 101 may be disposed between the first joined section 10g and the second joined section 10h.

In a sanitary napkin having a two-layered structure, if it is attempted to place a protection sheet after folding in the holding sections 32 towards the top absorbent body, the top face of the folded holding sections 32 is not flat due to the difference in level between the top absorbent body 20 and the base absorbent body 10 and does not bond well with the protection sheet, so that there is a risk that the shift-prevention attaching sections 33 are not formed properly in the holding sections 32. Therefore, before folding the holding sections 32 and the rear holding sections 39, a single protection sheet 74 is placed, from the back face side, on the back faces (top faces) of the holding section 32 and rear holding section 39 that are on the right side of the width direction. Then, a single protection sheet 75 is placed on the back faces of the holding section 32 and rear holding section on the left side. The holding sections 32 and rear holding sections 39 as well as the protection sheets 74 and 75 on the right and left sides are folded in towards the top absorbent body 20, and connected and integrated with adhesive at a portion where the protection sheets 74 and 75 are superposed near the center of the top absorbent body 20. In this manner, the shift-prevention attaching sections 33 and 71 are properly formed in the holding sections 32 and the rear holding sections 39.

SANITARY NAPKIN 5 OF THIRD MODIFIED EXAMPLE

Figure 16:
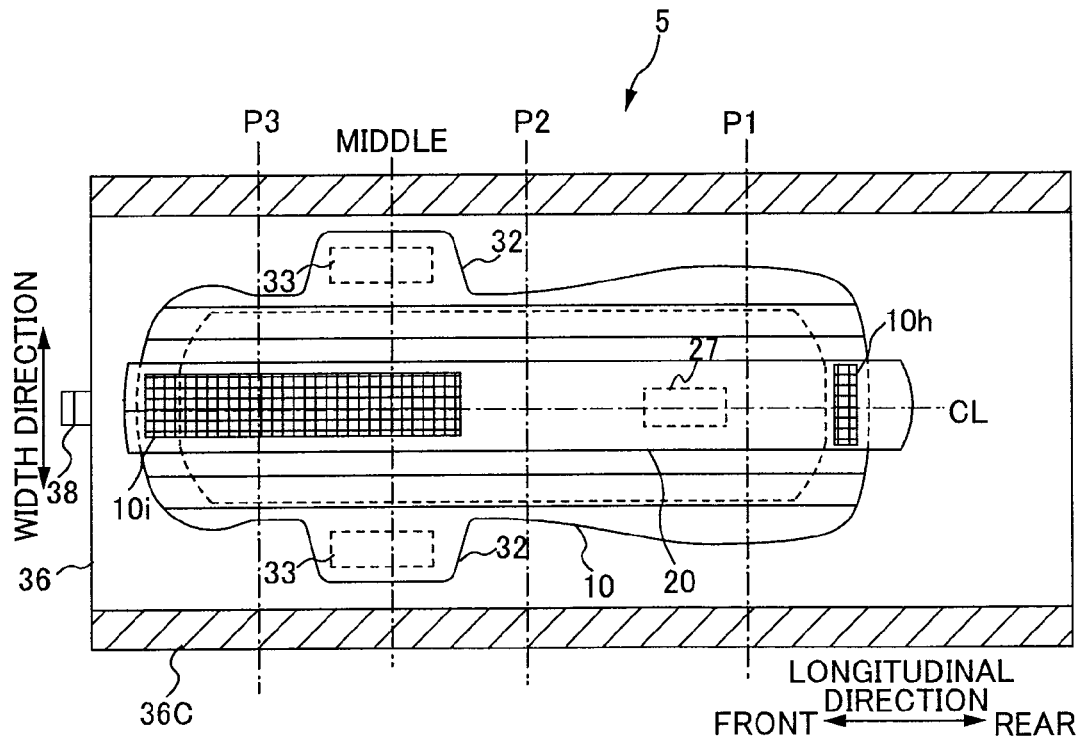
[FIG. 16] This is a diagram showing a sanitary napkin of the third modified example.

FIG. 16 shows a sanitary napkin 5 of the third modified example. In the sanitary napkin 5 of the third modified example, the length in the longitudinal direction of a first joined section 10i is longer than that of the above-described sanitary napkin 1 shown in FIG. 12A. In the sanitary napkin 5 of the third modified example, the top absorbent body 20 and the base absorbent body 10 are permanently joined up to a position close to the second folding position P2 beyond the middle between the second folding position P2 and the third folding position P3. In such a case, when the sanitary napkin 5 is folded at the second folding position P2, the first joined section 10i restricts the relative shifting between the top absorbent body 20 and the base absorbent body 10 in the front side with respect to the second folding position P2. Therefore, without holding the top absorbent body 20 between the protection sheet 35 and the base absorbent body 10 by folding the holding sections 32 in towards the top absorbent body 20, it is possible to prevent the top absorbent body 20 from shifting from the attachment position on the base absorbent body 10.

For this reason, if the temporary-joining restricting section 102 (fastening member 27) is disposed between the first folding position P1 and the second folding position P2, the holding restricting section 101 is not required to be disposed between the first joined section 10i and the second joined section 10h. However, the sanitary napkin can be packed smaller in the width direction if the holding sections 32 are folded in towards the top absorbent body 20. Also, to put it the other way around, in case of sanitary napkins that do not have the holding sections 32, if the top absorbent body 20 and the base absorbent body are permanently joined up to a position near the second folding position P2, it is possible to prevent the relative shifting between the top absorbent body 20 and the base absorbent body 10 when the sanitary napkin is folded at the second folding position P2, without separately providing a restricting member.

Second Embodiment

Figure 17:
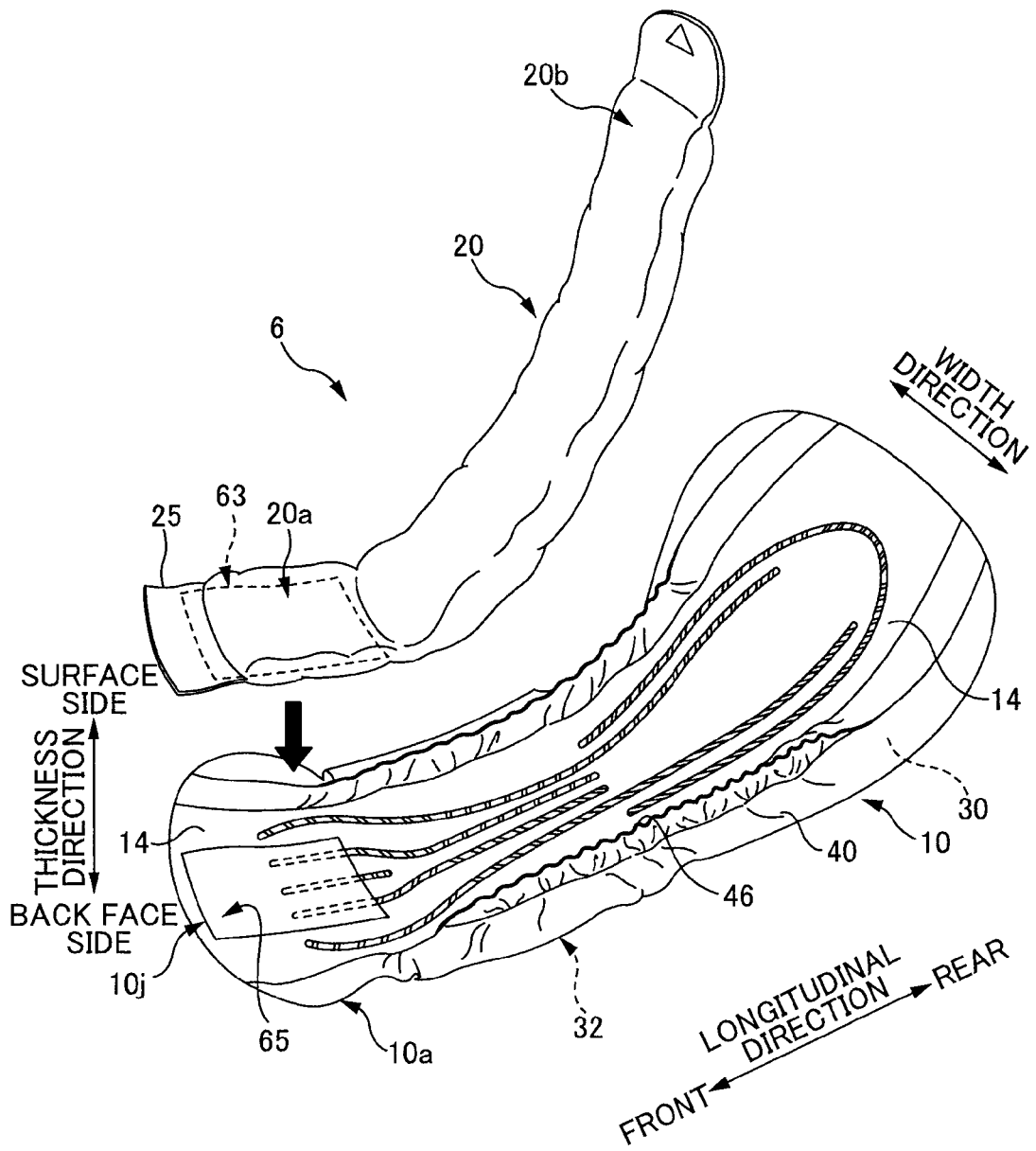
[FIG. 17] This is a perspective view of a sanitary napkin of the second embodiment.
Figure 18:
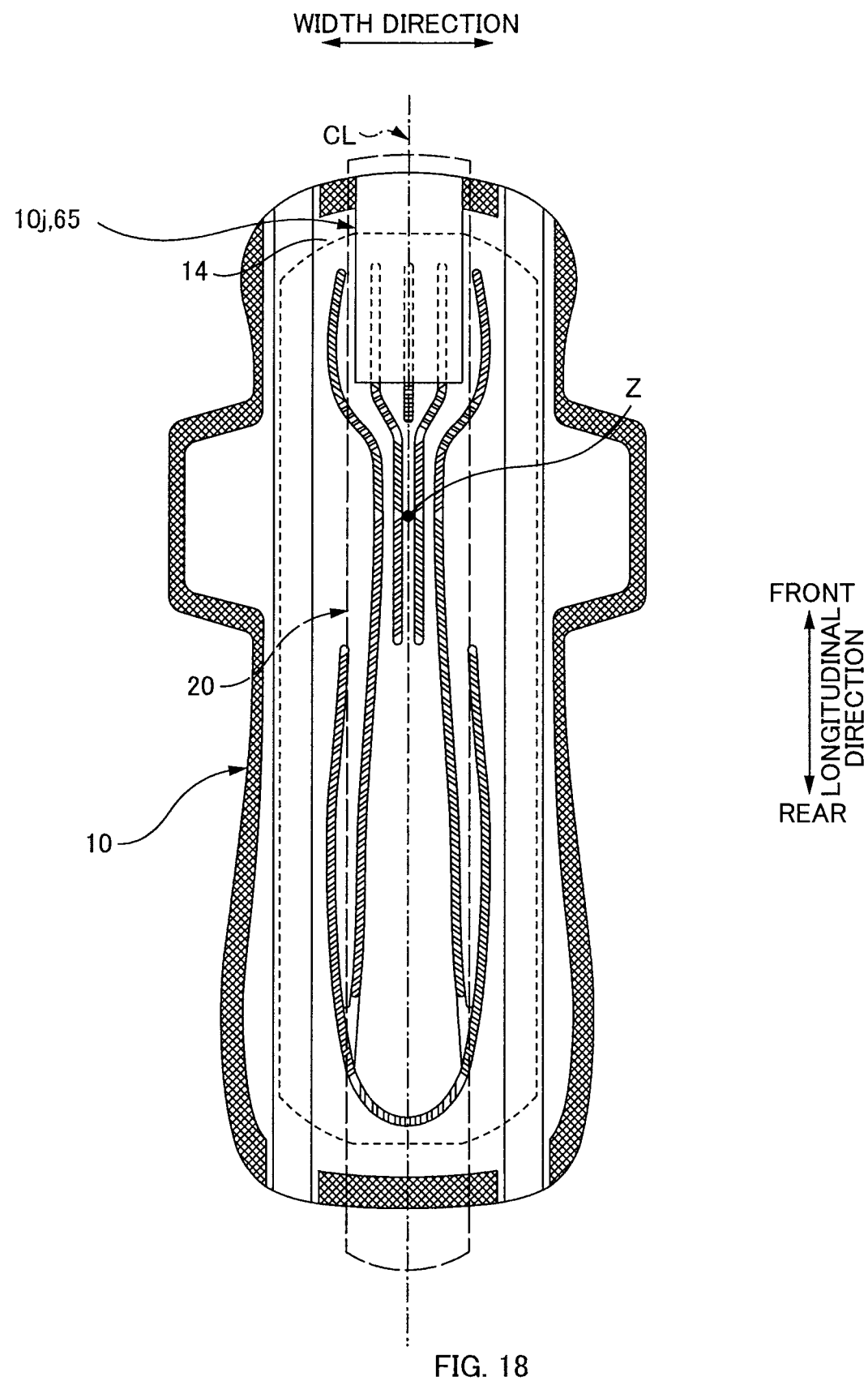
[FIG. 18] This is a plan view of the surface side of a base absorbent body.
Figure 19:
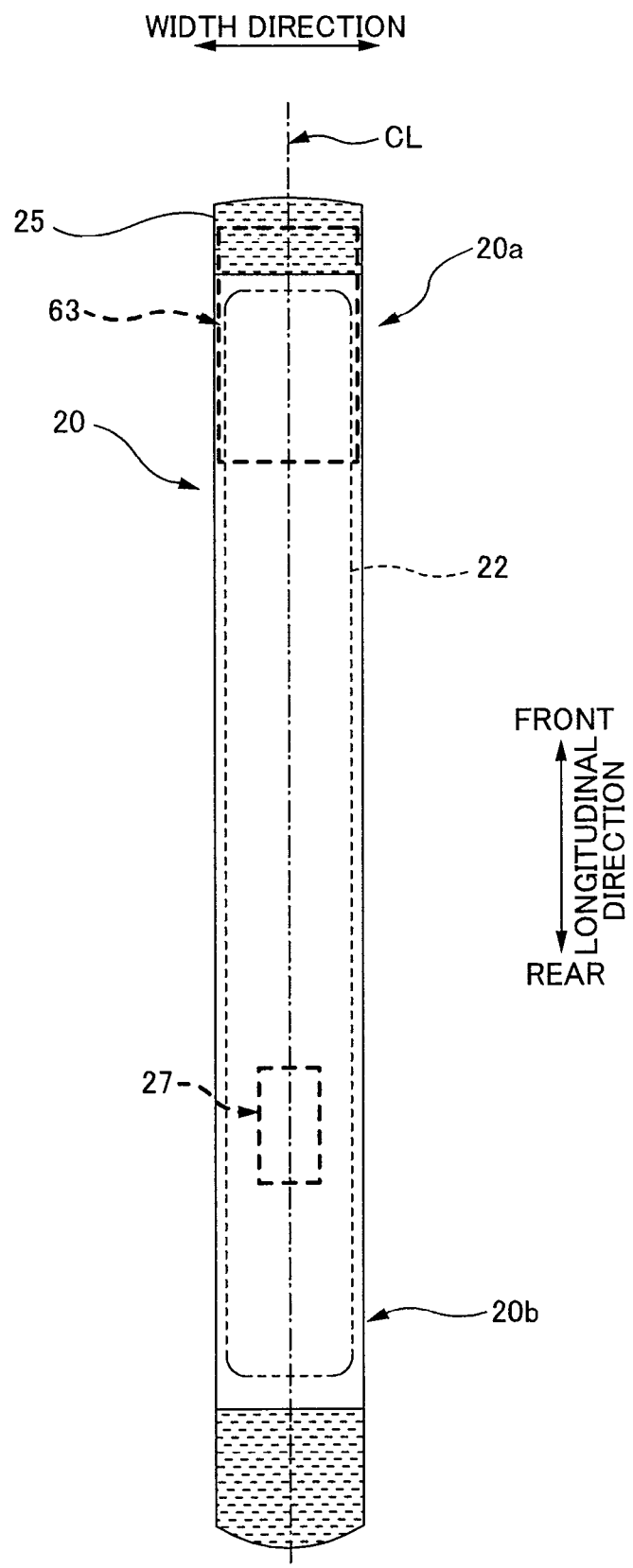
[FIG. 19] This is a plan view of the surface side of a top absorbent body.

FIGS. 17 to 19 show explanatory diagrams of an absorbent article 6 (e.g., sanitary napkin) of a second embodiment. FIG. 17 is a perspective view of the absorbent article 6 of the second embodiment. Also, FIG. 18 is a plan view of the surface side of a base absorbent body 10, and FIG. 19 is a plan view of the surface side of a top absorbent body 20. In FIG. 18, the contour of the top absorbent body 20 is indicated with a dotted line. In the foregoing embodiments, the top absorbent body 20 and the base absorbent body 10 are permanently joined in an inseparable manner at the permanently-joined section 10g; however, in the second embodiment, as shown in FIG. 17, the top absorbent body 20 and the base absorbent body 10 are made separable at a portion (hereinafter referred to as a "joined portion 10j") corresponding to the permanently-joined portion 10g (first joined section).

Specifically, as shown in FIGS. 17 to 19, although the planar size of the joined portion 10j and its position on the base absorbent body 10, etc. are the same as the permanently-joined section 10g of the foregoing embodiments, a female member 65 of a hook-and-loop fastener is fixed to the joined portion 10j and a male member 63 of the hook-and-loop fastener is fixed corresponding to the female member 65 on the back face side of the front end section 20a of the top absorbent body 20 (a front-side sealed section 25 and the rear side vicinity thereof). In this manner, the top absorbent body 20 and the base absorbent body 10 are detachable at the joined portion 10j.

The male member 63 of the hook-and-loop fastener is, for example, a rectangular sheet member with hook-like projections disposed on the entire surface thereof. More preferably, such projections are mushroom-shaped. This is because a fastening hook having the mushroom shape is not directional, and therefore can equally exhibit a high fastening force in any direction. As a result, when the top absorbent body 20 is joined to the base absorbent body 10 and the undergarment 90 is pulled up, the top absorbent body 20 is unlikely to detach from the base absorbent body 10 even if shaken horizontally to some extent.

In contrast, the female member 65 of the hook-and-loop fastener is, for example, a rectangular sheet member on the entire surface of which a large number of loops into which the projections of the male member 63 are hooked is formed. However, the female member 65 is not absolutely necessary. This is because it can be expected that fastening force works to some extent between the male member 63 of the top absorbent body 20 and the surface sheet 14 of the base absorbent body 10, which is formed of a nonwoven fabric. However, a nonwoven fabric having a good texture is normally used as a nonwoven fabric for the surface sheet 14 from the viewpoint of feel. In such a case, there is a risk that the entanglement strength of constituent fiber of the nonwoven fabric is week so that a joining strength is not sufficient. Therefore, it is desirable to fix the female member 65 to the joined portion 10j of the base absorbent body 10. Note that although the female member 65 is disposed in the base absorbent body 10 and the male member 63 is disposed in the top absorbent body 20, the female member 65 and the male member 63 may be disposed in the opposite manner.

Also, if pressure-sensitive adhesive is used instead of the hook-and-loop fasteners 63 and 65 in the joined portion 10j of the base absorbent body 10 and the front end section 20a of the top absorbent body 20, a sheet made of material from which the adhesive easily removes can be disposed corresponding to the region where the adhesive is applied. If pressure-sensitive adhesive is applied to at least either one of the joined portion 10j and the front end section 20a, the top absorbent body 20 and the base absorbent body 10 can be joined at the joined portion 10j.

That is, in the absorbent article 6 of the second embodiment, the base absorbent body 10 and the top absorbent body 20 are separable. When the base absorbent body 10 and the top absorbent body 20, each of which can be sold as a single product, are packed together for sale, the relative shifting between the base absorbent body 10 and the top absorbent body 20 can be restricted by temporarily joining the top absorbent body 20 and the base absorbent body 10 at the joined portion 10j (first joined section) and a second joined section 10h and arranging restricting members, which is the holding sections 32 and the fastening member 27, between the first joined section 10j and the second joined section 10h, as shown in FIGS. 12A to 12D for the foregoing embodiments. As a result, it is possible to prevent the top absorbent body 20 from shifting from the attachment position on the base absorbent body 10.

Also, with the absorbent article 6 of the second embodiment having such a separable configuration, when an absorbent article 6 has been used for a certain period of time and the top absorbent body 20 thereof has fully absorbed liquid, it is possible to replace only the top absorbent body 20 with another top absorbent body 20 that is individually wrapped and sold as a single product, without replacing the base absorbent body 10. Thus, in accordance with the reduction in frequency of replacing the base absorbent bodies 10, the amount of waste can be reduced. In such a case, since the base absorbent body 10 and the top absorbent body 20 are joined by a user of the absorbent article 6, a female member 65 having a color different from that of the surface sheet 14 is preferably used so that the joined portion 10j is visually-apparent. Thus, when the top absorbent body 20 and the base absorbent body 10 are joined, it is possible to prevent the joining position from shifting so that a joining strength is not sufficient.

When, instead of using the hook-and-loop fasteners 65 and 63, pressure-sensitive adhesive is applied to at least either one of the joined portion 10j and the front end section 20a, and the region where the adhesive is applied is covered by a sheet of release paper coated with release agent, and a user of the absorbent article 6 can peel the release paper to expose the adhesive, and join the base absorbent body 10 and the top absorbent body 20.

Other Embodiments

In the foregoing embodiments, while the front end side of the sanitary napkin is permanently joined and the rear end side is temporarily joined, there is no limitation to this. For example, the rear end side of the sanitary napkin may also be permanently joined. In addition, the front and rear end sides may be temporarily joined, and a portion near the holding sections 32 between the temporary-joined front and rear end sides may be permanently joined. In such a case, both the first and second joined sections are temporarily joined, and the permanently-joined portion near the holding sections 32 serves as the restricting member that restricts the relative movement between the top absorbent body 20 and the base absorbent body 10.

In the foregoing embodiments, both of the holding restricting section 101 and the temporary-joining restricting section 102 are formed between the first joined section 10g and the second joined section 10h. However, either one of the holding restricting section 101 and the temporary-joining restricting section 102 may be formed. For example, if a sanitary napkin does not have the holding sections 32, only the temporary-joining restricting section consisting of the fastening member 27 may restrict the relative shifting between the top absorbent body 20 and the base absorbent body 10. Conversely, if a sanitary napkin is such that the position of the top absorbent body 20 is fixed by being held without using the fastening member 27 by closely fitting the top absorbent body 20 into the groove section of the human body, only the holding restricting section may restrict the relative shifting between the top absorbent body 20 and the base absorbent body 10. If a sanitary napkin has neither the holding sections 32 nor the fastening member 27, a member (such as adhesive) that restricts the relative shifting between the top absorbent body 20 and the base absorbent body 10 may be disposed separately.

Also, in the foregoing embodiments, while the fastening member 27 is a member capable of re-joining, the fastening member 27 may be a member incapable of re-joining. However, in such a case, the fastening member 27 is used only for maintaining the position of the top absorbent body 20 in use, and cannot be used as the temporary-joining restricting section. Therefore another restricting member is required to be disposed between the first joined section and the second joined section.

Also, in order to function as the fastening member 27 used for the temporary-joining restricting section 102, adhesive may be applied to the top absorbent body, or the top absorbent body 20 and the base absorbent body 10 may be pressure-bonded by embossing.

In the foregoing embodiments, while the base absorbent body 10 serves as the main body section and the main body section includes an absorbent-body base material that absorbs liquid, there is no limitation to this. For example, the main body section does not have to include an absorbent-body base material, and may be formed of a fluid-impermeable member to prevent the liquid absorbed by the absorbent body (top absorbent body) from permeating to the undergarment 90.

The foregoing embodiments are for the purpose of elucidating the invention, and are not construed as limiting the invention in any way. The invention can be modified or improved without departing from the gist thereof, and any equivalents thereof are of course included in the scope of the invention.

The invention claimed is:

1. An absorbent article adapted to be worn by a user, said absorbent article comprising:
   a main body section;
   an absorbent body
      that includes an absorbent member for absorbing liquid,
      that has a longitudinal direction, a width direction, and a thickness direction,
      that is superposed on a user facing side of the main body section,
      that has a first end section in the longitudinal direction joined to the main body section at a first joined section, and
      that has a second end section opposite to the first end section in the longitudinal direction and joined to the main body section at a second joined section; and
   a restricting member
      that is disposed between the first joined section and the second joined section in the longitudinal direction, and
      that restricts a relative shifting between the main body section and the absorbent body when the main body section and the absorbent body are folded,
   wherein the main body section includes a holding section folded inwardly toward the absorbent body in the width direction, and
   wherein
   the absorbent article further comprises a sheet releasably bonded to a surface of the holding section on the user facing side of the main body section,
   the absorbent body is sandwiched between the sheet and the main body section, and
   the restricting member comprises portions of the sheet and the main body section that hold the absorbent body therebetween and restrict the relative shifting between the main body section and the absorbent body when the main body section and the absorbent body are folded.

2. An absorbent article according to claim 1, wherein the main body section and the absorbent body are folded at a folding position, which is between the first joined section and the restricting member, or between the second joined section and the restricting member.

3. An absorbent article according to claim 1, wherein
   a plurality of the restricting members are disposed between the first joined section and the second joined section in the longitudinal direction, and
   the main body section and the absorbent body are folded at a folding position that is between two of the plurality of restricting members in the longitudinal direction.

4. An absorbent article according to claim 1, wherein
   the restricting member comprises a temporary-joining restricting section that joins the main body section and the absorbent body in a re-joinable manner and that is disposed between the first joined section and the second joined section in the longitudinal direction.

5. An absorbent article according to claim 1, wherein
   the restricting member further comprises a temporary-joining restricting section that joins the main body section and the absorbent body in a re-joinable manner and that is disposed between the first joined section and the second joined section in the longitudinal direction,
   the portions of the sheet and the main body section that hold the absorbent body therebetween are disposed between the first joined section and the temporary-joining restricting section in the longitudinal direction,
   the absorbent article is folded at a middle folding position and an end-section folding position,
   the middle folding position is between the portions of the sheet and the main body section that hold the absorbent body therebetween and the temporary-joining restricting section in the longitudinal direction,
   the end-section folding position is between the temporary-joining restricting section and the second joined section in the longitudinal direction,
   the main body section and the absorbent body are folded at the end-section folding position before being folded at the middle folding position, and the temporary-joining restricting section is disposed closer to the end-section folding position than to a middle point between the middle folding position and the end-section folding position.

6. An absorbent article according to claim 1, wherein
the restricting member further comprises a temporary-joining restricting section that joins the main body section and the absorbent body in a re-joinable manner and that is disposed between the first joined section and the second joined section in the longitudinal direction,
the portions of the sheet and the main body section that hold the absorbent body therebetween are disposed between the first joined section and the temporary-joining restricting section in the longitudinal direction,
the absorbent article is folded at a middle folding position and an end-section folding position,
the middle folding position is between the portions of the sheet and the main body section that hold the absorbent body therebetween and the temporary-joining restricting section in the longitudinal direction,
the end-section folding position is between the temporary-joining restricting section and the second joined section in the longitudinal direction, and
the temporary-joining restricting section is disposed at a middle point between the middle folding position and the end-section folding position.

7. An absorbent article according to claim 4, wherein
the absorbent article is folded at a middle folding position and an end-section folding position,
the middle folding position is between the portions of the sheet and the main body section that hold the absorbent body therebetween and the temporary-joining restricting section in the longitudinal direction,
the end-section folding position is between the temporary-joining restricting section and the second joined section in the longitudinal direction, and
the portions of the sheet and the main body section that hold the absorbent body therebetween do not overlap the middle folding position and the end-section folding position.

8. An absorbent article according to claim 4, wherein
the absorbent article is folded at a middle folding position and an end-section folding position,
the middle folding position is between the portions of the sheet and the main body section that hold the absorbent body therebetween and the temporary-joining restricting section in the longitudinal direction,
the end-section folding position is between the temporary-joining restricting section and the second joined section in the longitudinal direction, and
the temporary-joining restricting section does not overlap the middle folding position and the end-section folding position.

9. An absorbent article according to claim 1, wherein a width of the main body section gradually increased from the holding section towards the second joined section,
the main body section further comprises another holding section opposite to the holding section in the longitudinal direction and folded inwardly toward the absorbent body in the width direction.

10. An absorbent article according to claim 9, wherein the sheet is further releasably bonded to a surface of said another holding section on the user facing side of the main body section.

11. An absorbent article according to claim 7, further comprising a wrapping sheet attached to the main body section on a garment facing side opposite to the user facing side of the main body section.

12. An absorbent article according to claim 11, wherein the wrapping sheet is folded at the middle folding position and the end-section folding position.

* * * * *